(12) United States Patent
Bills et al.

(10) Patent No.: US 7,198,619 B2
(45) Date of Patent: *Apr. 3, 2007

(54) VALVE SYRINGE

(75) Inventors: Dan J. Bills, Salt Lake City, UT (US);
Dan E. Fischer, Sandy, UT (US);
Bruce S. McLean, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 728 days.

This patent is subject to a terminal disclaimer.

(21) Appl. No.: 10/397,545

(22) Filed: Mar. 25, 2003

(65) Prior Publication Data

US 2003/0212372 A1 Nov. 13, 2003

Related U.S. Application Data

(63) Continuation-in-part of application No. 10/278,225, filed on Oct. 21, 2002, now Pat. No. 6,972,008, which is a continuation-in-part of application No. 10/106,397, filed on Mar. 26, 2002.

(51) Int. Cl.
*A61M 5/315* (2006.01)
(52) U.S. Cl. .................................... 604/218; 604/187
(58) Field of Classification Search ............... 604/110, 604/192, 218, 263, 187, 239, 264, 265, 275, 604/279, 193, 181
See application file for complete search history.

(56) References Cited

U.S. PATENT DOCUMENTS

| 1,831,668 | A | 11/1931 | Juhl | 128/214 |
|---|---|---|---|---|
| 2,261,213 | A | 11/1941 | Bierman | 128/214 |
| 3,277,922 | A | 10/1966 | Eisel | 137/613 |
| 4,043,336 | A | 8/1977 | Kreb, III | 128/218 R |
| 4,175,559 | A | 11/1979 | Kreb, III | 128/218 R |
| 4,679,705 | A | 7/1987 | Hamilton | 222/90 |
| 4,846,801 | A | 7/1989 | Okuda | 604/218 |
| 4,931,044 | A | 6/1990 | Beiter | 604/248 |
| 5,135,511 | A | 8/1992 | Houghton | 604/220 |
| 5,178,186 | A | 1/1993 | Levsseur | 137/556 |
| 5,814,017 | A | 9/1998 | Kashmer | 604/110 |
| 5,951,160 | A | 9/1999 | Ronk | 366/130 |
| 5,989,219 | A | 11/1999 | Villas | 604/110 |
| 6,972,008 | B2 * | 12/2005 | Bills | 604/218 |

\* cited by examiner

*Primary Examiner*—Manuel Mendez
(74) *Attorney, Agent, or Firm*—Workman Nydegger

(57) ABSTRACT

Valve syringes of the invention include a syringe barrel and an applicator valve adapted to rotate relative to the barrel between closed and open positions. In the open position, one or more slots in the applicator valve align with one or more holes in a discharge end of the syringe barrel in order to allow fluid material to flow therethrough. In a closed position, the contact surface of the applicator valve occludes the holes in the barrel in order to seal them and prevent flow of fluid material therethrough. The valve syringe may include structure that increases the sealing engagement between the syringe barrel and applicator valve when rotated toward at least one of the open or closed positions. The applicator valve may include an applicator tip that is either integrally or detachably connected to the applicator valve. The valve syringe may also include a plunger adapted to expel fluid material contained in the syringe barrel through the discharge end and into the applicator valve. An end of the plunger may be tapered or otherwise configured so as to conform to the shape of the discharge end of the syringe barrel.

25 Claims, 16 Drawing Sheets

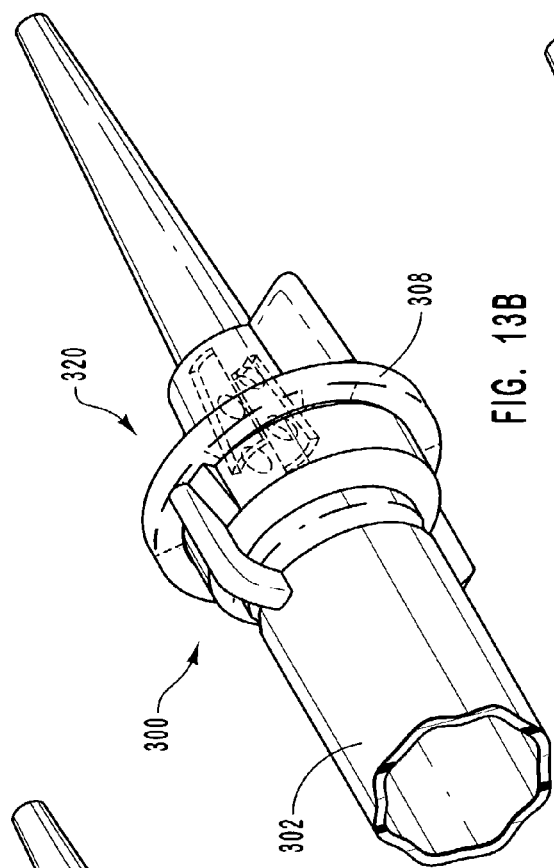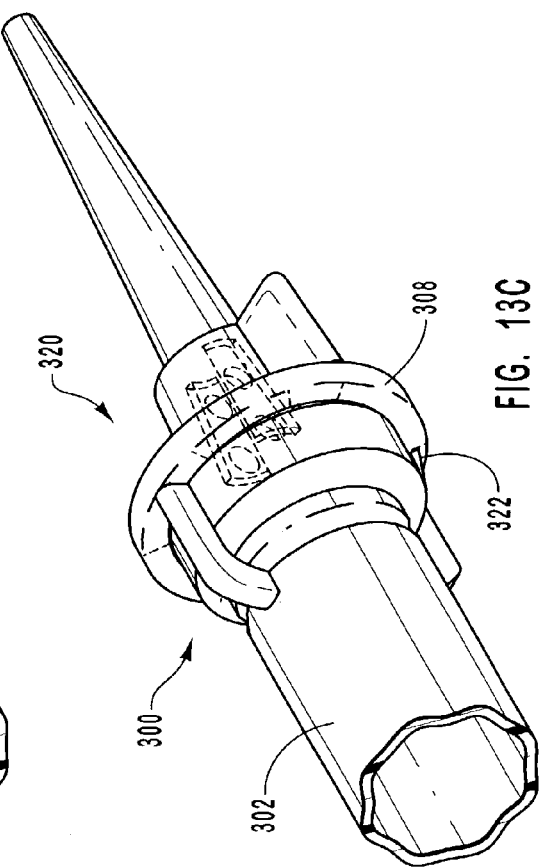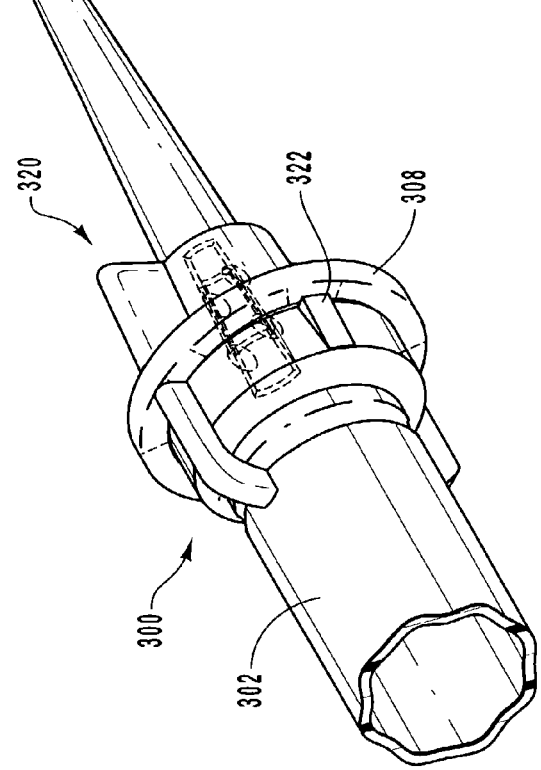

VALVE SYRINGE

CROSS-REFERENCE TO RELATED APPLICATIONS

This application is a continuation-in-part of U.S. application Ser. No. 10/106,397, filed Mar. 26, 2002, and entitled "Apparatus With Rotatable Valve Syringe", and also a continuation-in-part of U.S. application Ser. No. 10/278,225, filed Oct. 21, 2002 now U.S. Pat. No. 6,972,008, and entitled "Improved Syringe Having a Tapered Plunger". The foregoing applications are incorporated herein by reference in their entirety.

BACKGROUND OF THE INVENTION

1. The Field of the Invention

The present invention is in the field of dental composition delivery systems and, more particularly, in the field of dental syringes.

2. The Relevant Technology

In the field of dentistry, dental compositions are often delivered through a syringe. While some syringes contain only enough composition for a single application, other syringes contain enough composition to be used a plurality of times on a single patient or on a plurality of patients.

One benefit of multi-dose syringes, over the single dose syringes, is that they are generally more cost efficient. One drawback of multi-dose syringes, however, is that they are susceptible to cross-contamination. Another drawback includes the difficulty of ensuring the syringe is properly sealed between uses to prevent undesired leakage and evaporation or premature curing of the composition within the syringe. For instance, the tips of existing syringes are typically sealed closed with threaded or friction fitting caps. However, there is a risk the closure caps will not be sufficiently tightened onto the tips of the syringes between uses because the existing syringes do not include means for indicating when the caps are sufficiently sealed or tightened onto the tips of the syringes. Yet another problem with multi-dose syringes is that the syringe caps or lids can easily be misplaced or lost, thereby preventing the syringes from being adequately sealed. When the cap is not sufficiently sealed on the tip of a syringe then the composition within the syringe can leak, evaporate, or prematurely cure, thereby minimizing the cost advantage of purchasing the larger capacity multi-dose syringes.

Single dose syringes provide an improvement over the multiple dose syringes for at least minimizing the risk of cross-contamination. However, single dose syringes can also be susceptible to undesired leakage and evaporation or premature curing of the dental composition contained therein. In particular, the closure caps placed over the tips of existing single dose syringes can become dislodged during shipping, storage, and other periods of nonuse, thereby enabling the composition to leak or evaporate.

Accordingly, in view of the foregoing, there is currently a need in the art for improved syringe delivery systems and, more particularly, to syringe delivery systems that are configured to reduce leakage and evaporation, or premature curing during shipping, storage, and other periods of nonuse.

SUMMARY OF PREFERRED EMBODIMENTS

Briefly summarized, presently preferred embodiments of the present invention are directed to improved syringe delivery systems.

According to one embodiment, the valve syringe of the invention includes a syringe barrel configured for containing a fluid material, a plunger slidably disposed within the syringe barrel and configured for pushing the fluid material to an outlet end of the barrel, and an applicator valve disposed at the outlet end of the barrel that is also configured to rotate between an open position and a closed position for controlling the flow of the fluid material through the applicator valve.

In one embodiment according to the invention, the applicator valve includes an inner contact surface configured to frictionally engage a tapered outlet end of the syringe barrel for preventing the fluid material from flowing through at least one opening formed in the outlet end of the barrel when the applicator valve is in the closed position. The applicator valve also includes at least one relief slot formed in the inner contact surface that is configured to allow the fluid material to flow through the one or more barrel openings when the applicator valve is in the open position. When the applicator valve is in the open position, the fluid material is able to flow through the applicator valve and into an applicator Utip through which the fluid material can dispensed to a desired location.

The applicator tip, which may be specifically configured to dispense a particular composition contained in the syringe barrel, may comprise at least one of a cannula, a needle, a curved hollow body, a flocked applicator tip, or a tip of any desired configuration. In one embodiment, the applicator tip may be integrally connected to the applicator valve. In another embodiment, the applicator tip may be detachably coupled with the applicator valve, such as with threaded surfaces, a compression fit, a snap fit, or other coupling means known in the art.

In one embodiment, the valve syringe further includes securing means for releasably securing the applicator valve in the closed position during periods of nonuse. Securing means are useful for helping to prevent inadvertent rotation of the applicator valve into the open position during shipping, storage, and other periods of nonuse. Securing means may include any engagement formation configured to resist rotation of the applicator valve from the closed position. In one embodiment, the securing means includes knobs and recesses, wherein the knobs are configured to mate within the recesses only when the applicator valve is in the closed position, thereby resisting rotation of the applicator valve from the closed position. The valve syringe may also include securing means for releasably securing the applicator valve in the open position to prevent inadvertent closure of the valve during use.

The applicator valve may also include rotation facilitating means for facilitating rotation of the applicator valve between the open and closed positions, notwithstanding the presence of any securing means. In one embodiment, the rotation facilitating means includes protruding wing members extending from the applicator valve. The protruding wing members are specifically configured to be engaged by the fingers of a user and generally increase the leverage that can be applied for rotating the applicator valve.

To prevent over-rotation of the applicator valve, the valve syringes also include stopping means for stopping rotation of the applicator valve in the open position when the applicator valve is rotated in a first direction and for stopping rotation of the applicator valve in the closed position when the applicator valve is rotated in the opposite direction. According to one embodiment, the stopping means includes at least one radial block member protruding away from the applicator valve and configured to engage the tab members once the applicator valve is completely rotated into either one of the open and closed positions.

The applicator valve may be secured on the end of the syringe barrel by retaining means which, according to one embodiment, includes a ridge member circumferentially extending at least partially around the applicator valve and at least one tab member extending from the syringe barrel. The at least one tab member slidably engages the at least one ridge member while the applicator valve is rotated between the open and closed positions, thereby retaining the applicator valve at the exit end of the syringe barrel.

Alternatively, the retaining means may comprise one or more (e.g., 2) lateral protrusions extending from an end of the applicator valve and a circumferential retention ring at an end of the barrel that slidably engages the one or more lateral protrusions of the applicator valve to retain the applicator valve over the outlet end of the barrel. In this embodiment, the lateral protrusions of the applicator valve slidably engage an engagement surface of the circumferential retention ring in order to prevent separation of the applicator valve from the syringe barrel. The slidable engagement of the lateral protrusions and the engagement surface allows the applicator valve to be rotated relative to the syringe barrel between the opened and closed positions.

In one embodiment, the circumferential retention ring is spaced apart from the outlet end of the barrel by a circumferential gap through which two lateral protrusions on the applicator valve are inserted during initial assembly of the valve syringe. In this embodiment, the circumferential retention ring is attached to the syringe barrel by a pair of attachment ridges extending from a surface of the outlet end of the barrel and spaced-apart by 180°. The attachment ridges may also act as stopping means, which engage the lateral protrusions on the applicator valve, in order to limit rotation of the applicator valve. In one embodiment, the lateral protrusions of the applicator valve will selectively abut one side of the attachment ridges when the applicator valve is turned to the completely open position, and the lateral protrusions will abut the other side of the ridges when the applicator valve is turned to the completely closed position, thereby comprising stopping means.

The valve syringe may optionally comprise means for varying the tightness of the sealing engagement between the applicator valve and the outlet end of the syringe barrel when the applicator valve is rotated between the open and closed positions. In one embodiment this comprises a stepped, angled or otherwise varying engagement surface on the circumferential retention ring that engages the lateral protrusions of the applicator valve with varying force as the valve is rotated between the open and closed positions. In this embodiment, the applicator valve is pulled with more or less retention force against the outlet end of the syringe barrel depending on the location of the lateral protrusions relative to the engagement surface.

In one embodiment, the engagement surface of the circumferential retention ring includes a lower middle region, which exerts the least retention force onto the lateral protrusions of the applicator valve when the applicator valve is positioned intermediate between the completely opened and closed positions, and inclined regions on either side of the middle region that progressively exert increasing retention force onto the lateral protrusions as the applicator valve is rotated toward either the closed or open position. The inclined regions may extend all the way from the lower middle region to the attachment ridges, or they may terminate at level or stepped regions adjacent to the attachment ridges. In the latter embodiments, the lateral protrusions of the applicator valve may rest on the level or stepped down regions whenever they abut the attachment ridges (i.e., whenever the applicator valve is in the completely open or closed position). In this way, the level regions, and particularly the stepped down regions where present, may comprise an embodiment of the aforementioned securing means.

In one embodiment, the valve syringe may also include tamper evident means for indicating whether the applicator valve has rotated from the closed position to the open position at least one time. The tamper evident means may include a flange, a bridge, or any other physical coupling between the applicator valve and the barrel of the syringe. When the applicator valve is rotated from the closed position to the open position for the first time, the tamper evident means is visually and irreversibly broken.

In one embodiment, the valve syringe includes a barrel having a tapered outlet end that also includes an inner surface that defines a tapered void. In order to accommodate a tapered inner portion of the syringe barrel, the plunger may optionally be configured with a tapered end that is sized and shaped to conformingly engage the inner surface of the tapered portion of the barrel. This configuration enables the plunger to facilitate expulsion of substantially all of the fluid material that may reside within the tapered portion of the barrel.

The plunger may optionally include sealing means for sealing the stem of the plunger against an inner surface of the barrel. Such sealing means effectively prevents leaking and undesired loss of the fluid material between the plunger and the barrel. According to one embodiment, the sealing means includes one or more flexible sealing rings that circumferentially protrude away from the stem proximal to a forward end of the plunger. The sealing rings are preferably configured to slidably engage the inner surface of the barrel so as to prevent leaking of the fluid material between the stem and the barrel.

During use, the plunger is forced through the barrel, causing the fluid material to be expelled out of the one or more openings formed in the outlet end of the syringe barrel. In the case where the syringe barrel includes an inner surface that defines a tapered void, the plunger may optionally include a tapered end as discussed above to help fully expel the fluid material out of the barrel when the tapered plunger end is inserted into the tapered void defined by the tapered outlet end of the syringe barrel.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings, in which:

FIG. 13A is a perspective view of the syringe barrel and applicator valve of FIG. 12 joined together, with the lateral protrusion of the applicator valve being positioned midway between the attachment ridges;

FIG. 13B is a perspective view of the joined syringe barrel and applicator valve of FIG. 13A, with the applicator valve rotated to the closed position in which the lateral protrusion abuts one of the attachment ridges; and FIG. 13C is a perspective view of the joined syringe barrel and applicator valve of FIG. 13A, with the applicator valve rotated to the open position in which the lateral protrusion abuts the other attachment ridge.

DETAILED DESCRIPTION OF THE PREFERRED EMBODIMENTS

A detailed description of the valve syringe of the invention will now be provided with specific reference to figures illustrating preferred embodiments of the invention. It will be appreciated that like structures will be provided with like reference designations.

In order to provide context for interpreting the scope of the invention, certain terms will now be defined. The term "composition," as used herein, refers to any fluid material or fluid composition of materials capable of being dispensed through a syringe. By way of example and not limitation, the compositions referred to herein include organic and synthetic compositions as well as water-based and solvent-based compositions. Although the terms "composition" and "fluid material" are used interchangeably herein, it will be appreciated that the compositions and fluid materials are not limited to having any particular viscosity. Rather the viscosity of the fluid materials can vary to accommodate different needs and preferences, but should be at least low enough to flow through the applicator valve and applicator tip during normal use.

The term "applicator tip," as defined herein, refers to any tip, tube, needle, cannula, or other dispensing device configured to dispense a fluid material and is characterized by the attribute of including at least a hollow or concave portion through which the fluid material can flow.

The term "luer taper," as used herein, refers to a standard luer taper of about six v, percent (6%) as described in document "ISO 594-2: 1998 Conical fittings with 6% (Luer) taper for syringes, needles and certain other medical equipment—Part 2: Lock fittings." However, it will be appreciated that the luer taper may also comprise other angles that are either less than or greater than six percent as desired.

The term "mating engagement formations," as defined herein, refers to any combination of engaging formations, including, but not limited to, recesses, ridges, protrusions, holes, latches, clips, knobs, pins, slots, tabs, rings and apertures which are configured to interconnect, internest, mate, lock, or otherwise mechanically engage.

The valve syringes of the invention, as described herein, are generally configured to control the flow of fluid material through an application valve disposed at the outlet end of a syringe barrel. During use, fluid material flowing through the application valve is dispensed through an application tip, which is either integrally connected to or detachably connected with the applicator valve.

Figure 1:
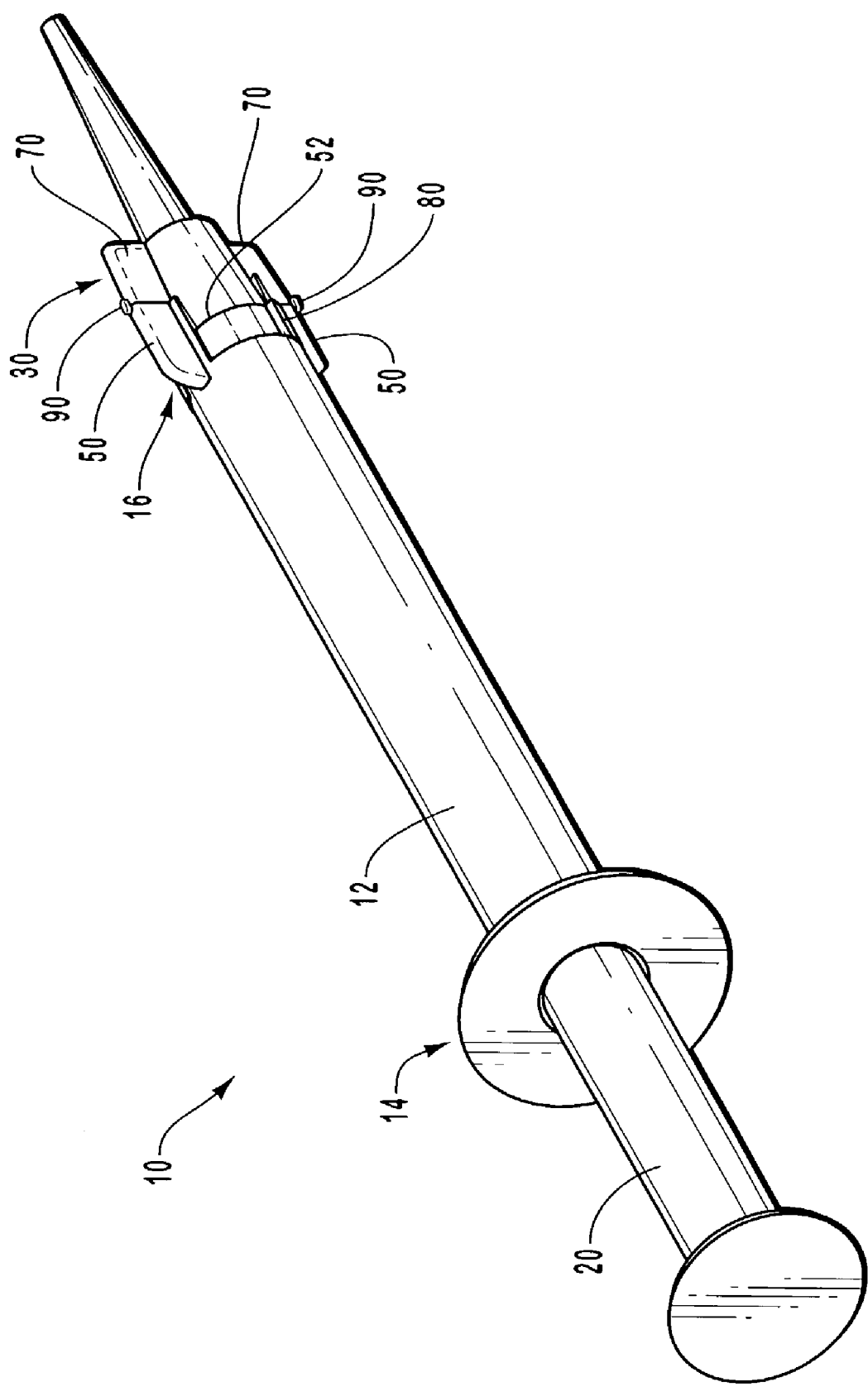
FIG. 1 is a back perspective view illustrating an embodiment of a valve syringe that includes a barrel configured for containing a fluid material, a plunger configured for pushing the fluid material to the outlet end of the barrel, and an applicator valve disposed at the outlet end of the barrel.

FIG. 1 illustrates one presently preferred embodiment of the valve syringe 10 of the invention. As shown, the valve syringe 10 generally includes a barrel 12 configured for containing a fluid material. The barrel 12 has a generally cylindrical cross-sectional shape and extends from an inlet end 14 to an outlet end 16. It will be appreciated that the cross-sectional shape of the barrel 12 may vary to accommodate various needs and preferences. The plunger 20, inserted within the inlet end 14 of the barrel 12, is specifically configured in shape and size for pushing the fluid material contained within the barrel 12 to the outlet end 16 of the barrel 12, where it is forced through and dispensed out of the applicator valve 30. The applicator valve 30 is preferably configured in size and shape for rotatably engaging the outlet end 16 of the barrel 12.

Figure 2:
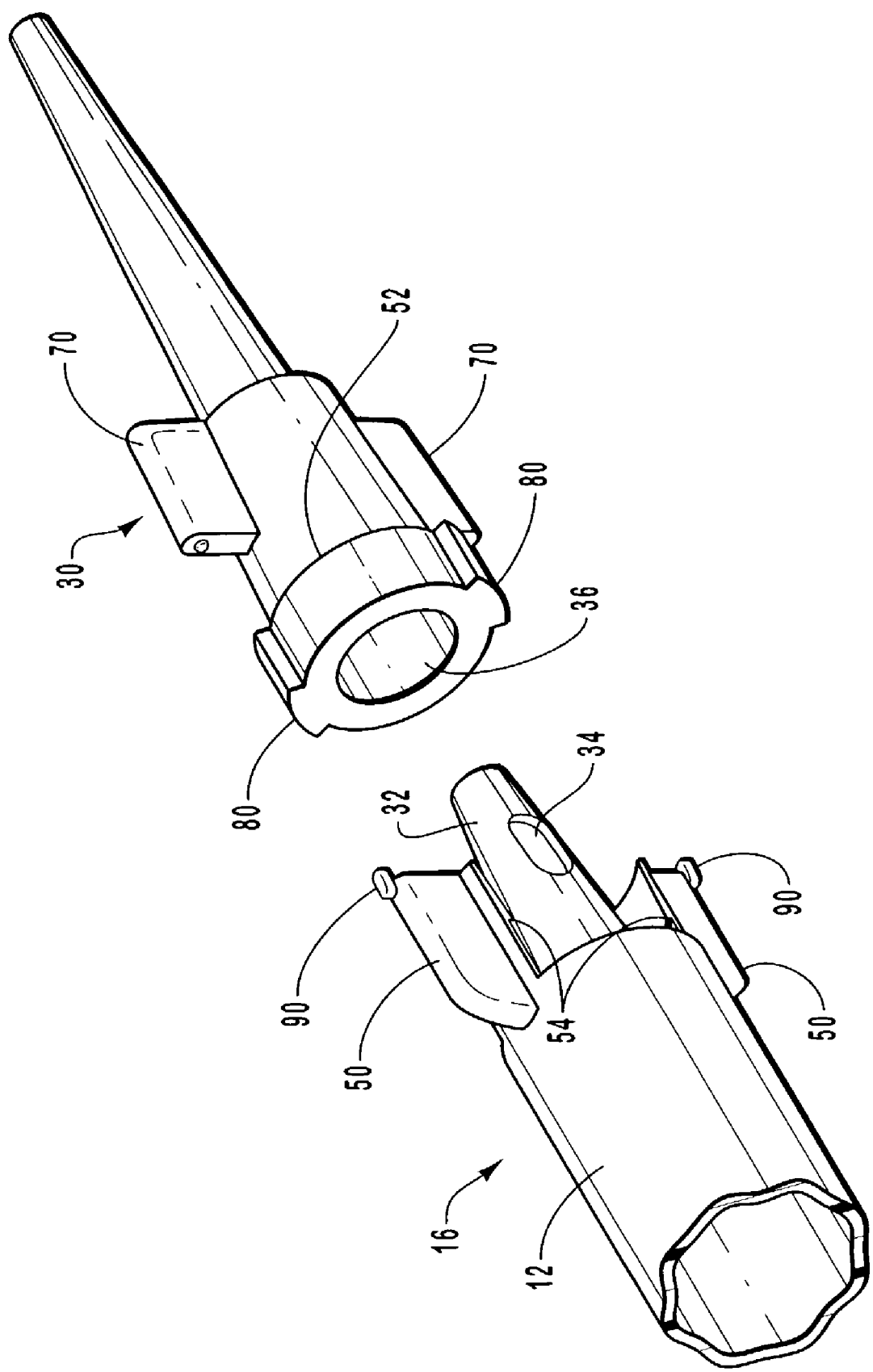
FIG. 2 is an exploded perspective view depicting the outlet end of the barrel and the applicator valve of the valve syringe of FIG. 1.

FIG. 2 illustrates an exploded view of the applicator valve 30 and the outlet end 16 of the barrel 12. As shown, the outlet end 16 of the barrel 12 includes a sidewall 32 with at least one barrel opening 34 formed in the sidewall 32. The sidewall 32 is preferably tapered, such as with a standard 6% luer taper. It will be appreciated, however that the angle of the taper may vary to accommodate different needs and preferences.

According to one present embodiment, the valve syringe 10 includes two barrel openings 34 that are disposed in opposite sides of the sidewall 32, although only one of the barrel openings 34 can be seen in the illustration shown. In other embodiments, only a single opening 34 is present.

According to the preferred embodiment, the applicator valve 30 includes a contact surface 36 that is correspondingly tapered to abuttingly engage the outlet end 16 of the barrel 12. In particular, the contact surface 36 of the applicator valve 30 is configured in size and shape to engage the sidewall 32 of the outlet end 16 of the barrel 12 so as to prevent the fluid material from exiting through the barrel openings 34 when the applicator valve 30 is disposed in a closed position, as generally shown and described below in reference to FIG. 3.

Figure 3:
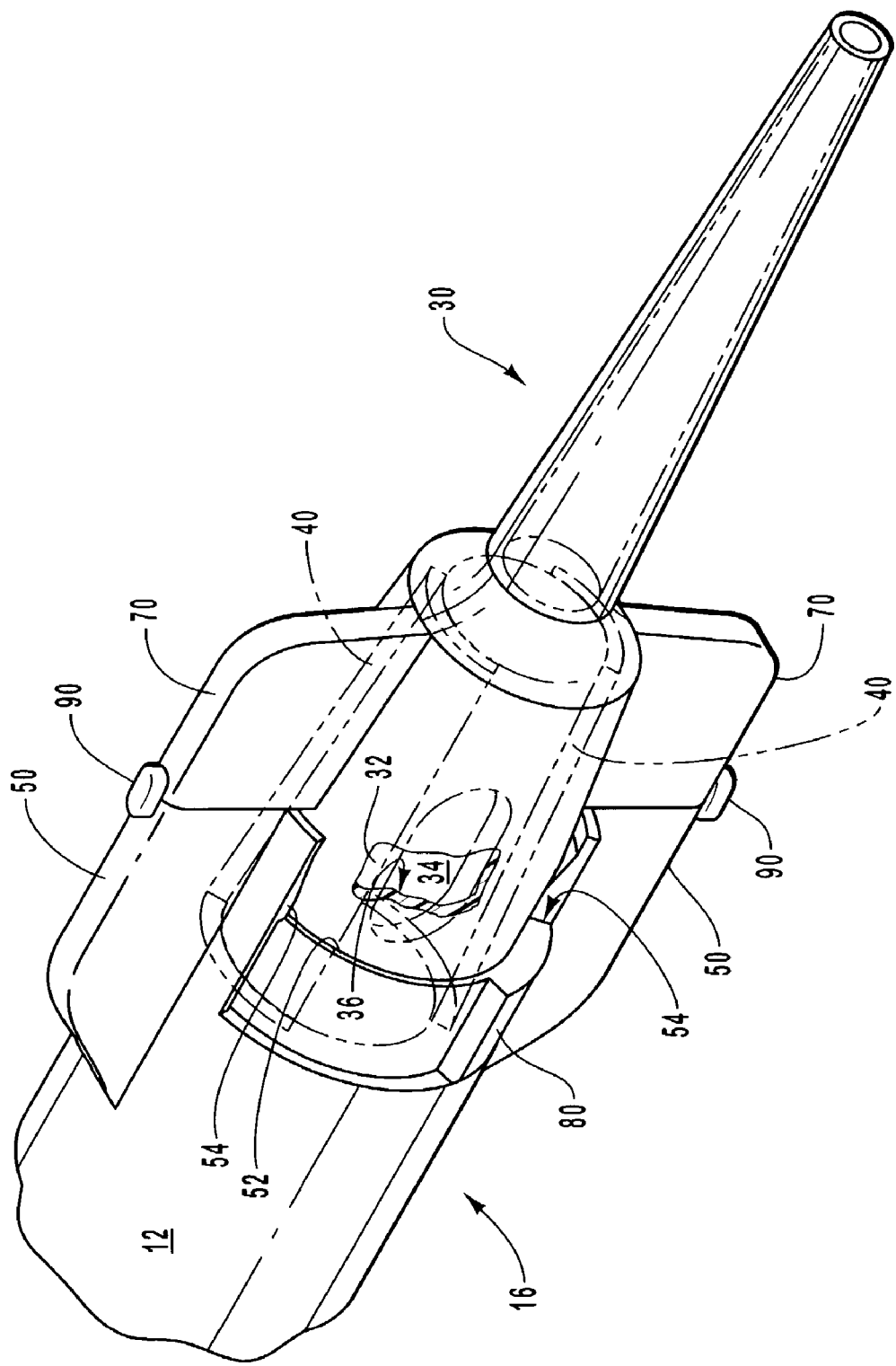
FIG. 3 is a partial cross-sectional perspective view of the outlet end of the barrel and the applicator valve of the valve syringe of FIG. 1 with the applicator valve disposed in the closed rotational position.

FIG. 3 illustrates a partial cross-sectional perspective view of the applicator valve 30 disposed on the outlet end 16 of the barrel 12 in a closed position. As shown, in the closed position, the contact surface 36 of the applicator valve 30 covers the barrel opening to prevent the fluid material from passing therethrough.

Figure 4:
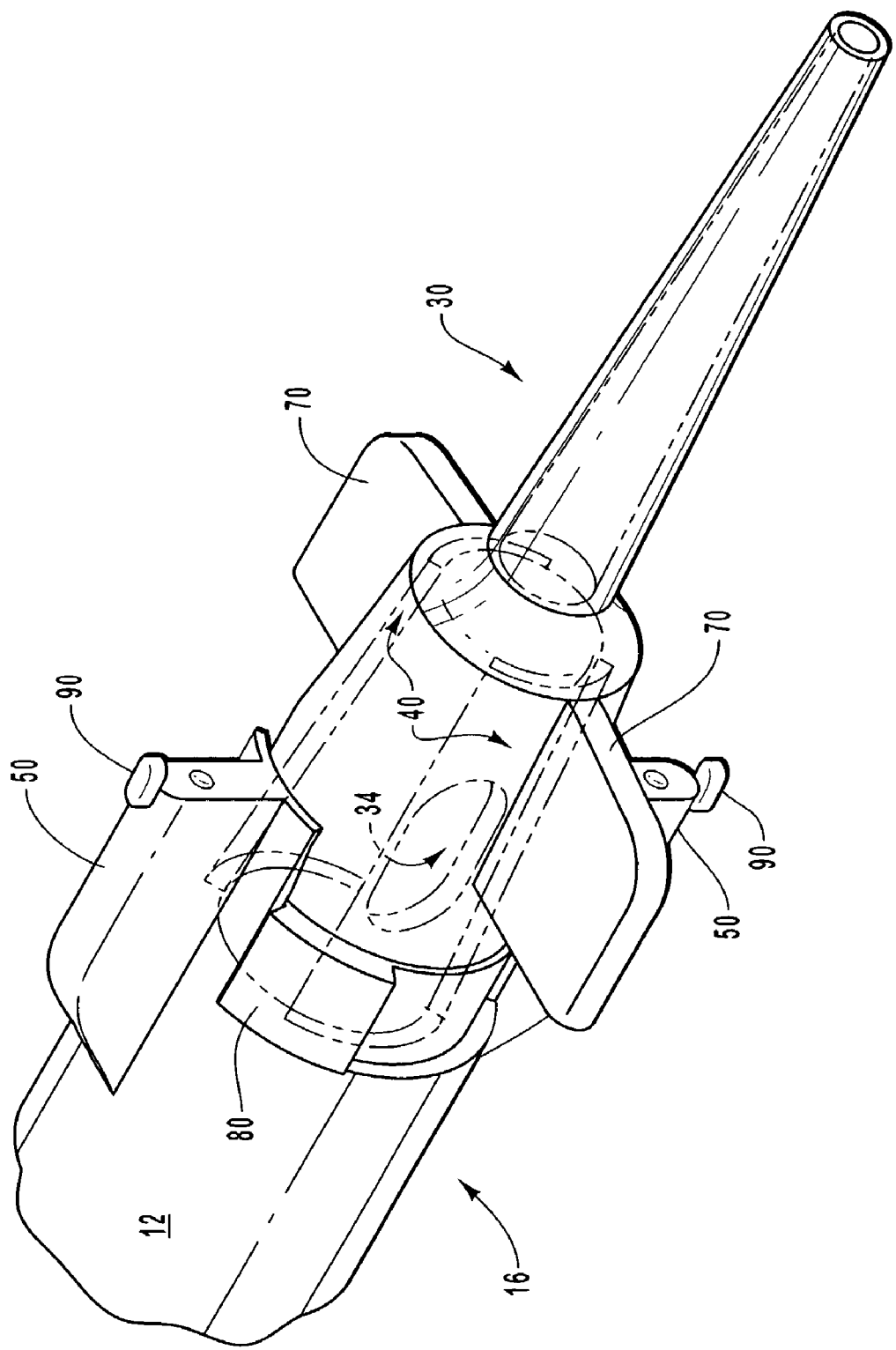
FIG. 4 is a front perspective view of the outlet end of the barrel and the applicator valve of the valve syringe of FIG. 1 with the applicator valve disposed in the open rotational position.

FIG. 4 illustrates the applicator valve 30 in an open position. As shown, relief slots 40 formed within the contact surface 36 of the applicator valve 30 at least partially align with the barrel openings 34 in the outlet end 16 of the barrel 12, although only one barrel opening 34 is presently visible in this view. This arrangement of the relief slots 40 and the barrel openings 34 is further clarified by the illustration shown in FIG. 5.

Figure 5:
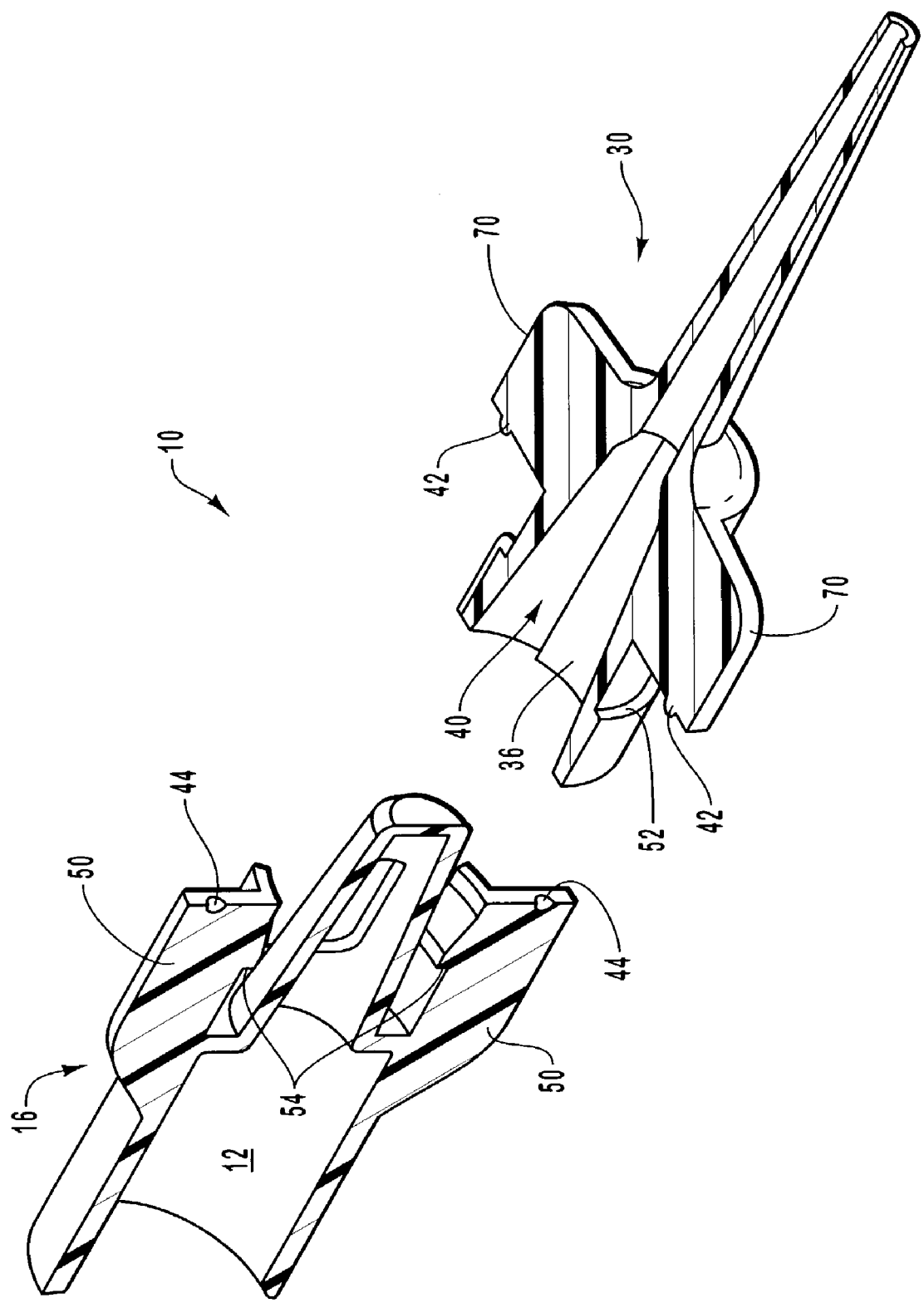
FIG. 5 is a cross-sectional exploded view of the outlet end of the barrel and the application valve of the valve syringe of FIG. 1 showing the alignment of the barrel opening and the relief slot when the application valve is rotationally aligned in the open position.

FIG. 5 illustrates an exploded cross-sectional view of the outlet end 16 of the barrel 12 and of the applicator valve 30. As shown, the applicator valve 30 is concentrically aligned with the barrel 12 and rotated with respect to the barrel in the rotational alignment of the open position shown in FIG. 4. It is evident that when the applicator valve 30 is disposed on barrel 12 in this rotational alignment, within an open position, that the barrel opening 34 at least partially aligns with the relief slot 40 formed into the contact surface 36 of the applicator valve 30. It should also be appreciated that by aligning the barrel opening 34 with the relief slots, in the open position, that the composition within the barrel will be able to flow through the barrel openings 34 and into the applicator valve through which it is dispensed during use. Flow can occur even when the openings are only partially aligned, although some restriction may occur depending on the degree of alignment.

FIG. 5 also illustrates securing means for releasably securing the applicator valve 30 in the closed position. In particular, knobs 42 and recesses 44 formed in the valve syringe 10 are configured to internest in mechanical engagement when the applicator valve 30 is disposed in the fully closed position, which is shown and described above in reference to FIG. 3. The securing means may also include any other combination of mating engagement formations, including, but not limited to, recesses, ridges, protrusions, holes, latches, clips, knobs, pins, slots, tabs, and apertures which are configured to interconnect, internest, mate, lock, or otherwise mechanically or frictionally engage when the applicator valve 30 is in the closed position.

It will be appreciated that the securing means of the invention are useful for at least enabling a user to know when the applicator valve 30 is completely rotated into the closed position. In this manner, the valve syringes 10 of the invention provide an improvement over prior art devices which include closure caps that do not have any means for indicating when the cap is sufficiently placed over the syringe to prevent the flow or evaporation of the fluid material contained therein. Instead, prior art devices require the user to repeatedly determine how tightly the closure cap must be placed on the syringe to prevent undesired leaking and evaporation of the fluid material contained within the syringe. In contrast, the securing means of the present invention enable a user to know exactly how far the applicator valve 30 must be rotated to secure the applicator valve 30 in the closed position. Once in the closed position, the securing means also prevent the applicator valve 30 from being inadvertently rotated into the open position. In this manner the securing means of the invention also provide an improvement over prior art devices that include closure caps that can easily become dislodged or unsecured during shipping, storage, and other periods of nonuse.

FIGS. 1–5 also illustrate retaining means for retaining the applicator valve 30 on the outlet end 16 of the barrel 12. In these presently shown embodiments, the retaining means includes tab members 50 extending from the outlet end 16 of the barrel 12 and a ridge member 52 circumferentially extending at least partially around the applicator valve 30. As shown, each of the tab members 50 includes a ledge 54 configured to slidably engage the ridge member 52 of the applicator valve 30 during rotation of the applicator valve 30 between the open and closed positions. In this manner the valve syringe 10 of the invention provides means for retaining the applicator valve 30 at the outlet end 16 of the barrel 12. It will be appreciated, however, that the applicator valve 30 can still be removed from the outlet end 16 of the barrel 12 by flexing the tab members 50 away from the barrel 12 until the ledges 54 clear the ridge member 52. This is useful, for instance, to enable the applicator valve 30 to be interchanged. It may be desirable to interchange the applicator valve 30 when the sanitation of the applicator valve 30 is compromised, such as may occur when the valve syringe 10 is dropped on the floor, or placed in a patient's mouth, for instance.

Figure 6:
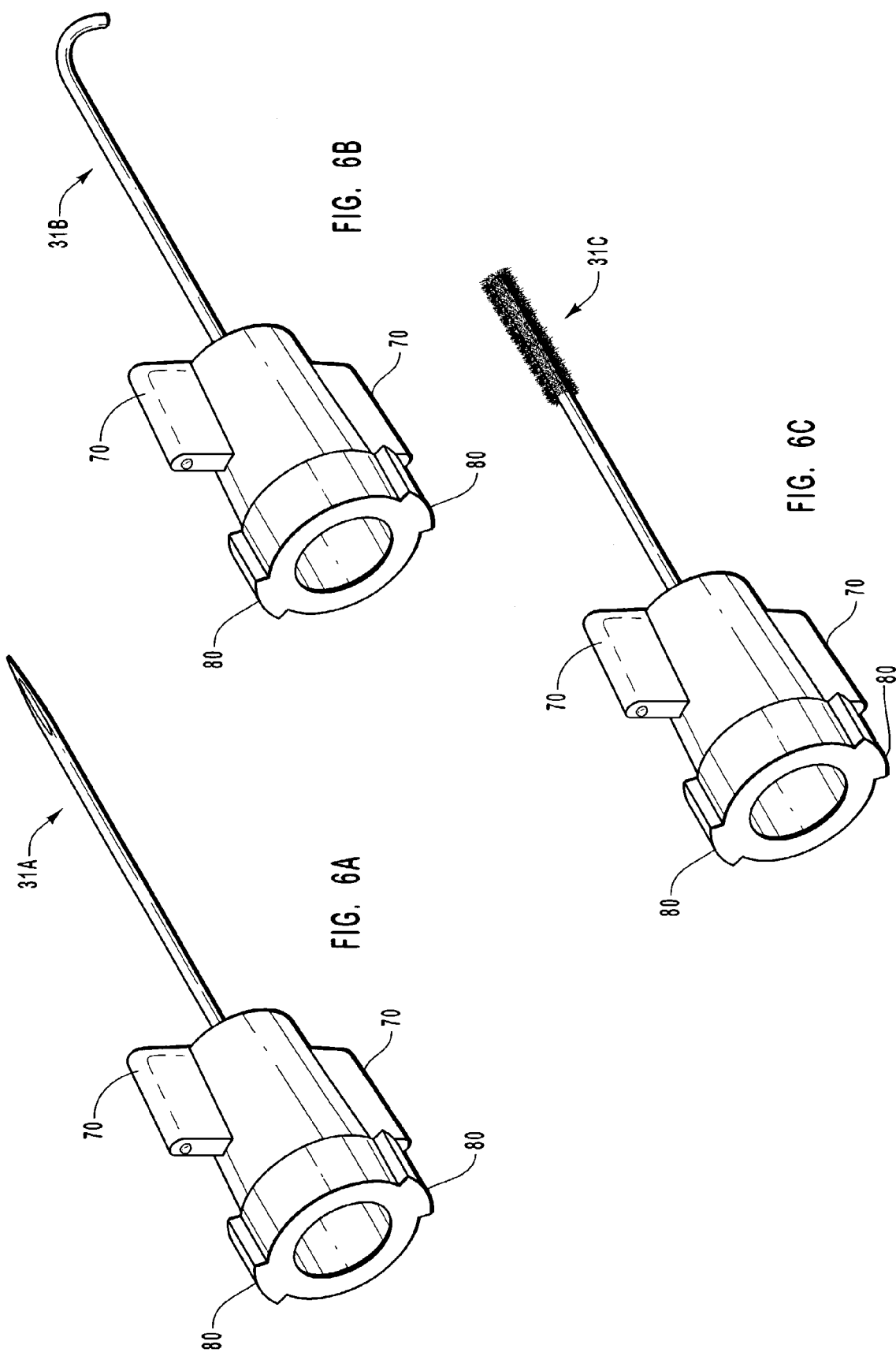
FIG. 6A is a perspective view of an embodiment of an applicator valve of the invention that includes an applicator tip configured as a needle.
FIG. 6B is a perspective view of an embodiment of an applicator valve of the invention that includes an applicator tip configured as a curved cannula.
FIG. 6C is a perspective view of an embodiment of an applicator valve of the invention that includes a flocked applicator tip.

Although the barrel 12 of the valve syringe 10 can be configured for containing only enough composition for a single use, it can also be configured with a sufficiently large barrel 12 to contain multiple doses of the composition, in which case it is also desirable to interchange the applicator valve 30 between uses on different patients. It may also be desirable to interchange the applicator tip between uses on a single patient if a two-part composition has mixed and cured within the applicator tip. Yet another reason to interchange the applicator valve 30 is to utilize the special attributes of differently shaped and configured applicator tips. For instance, the applicator tip may be configured as a needle applicator 31A, as a cannula applicator 31B, or as a flocked applicator 31C, as shown in FIGS. 6A–6C to accommodate different needs and preferences.

In one embodiment (not shown) the securing means is configured so as to prevent the applicator valve 10 from being removed at all. For instance, in this alternative embodiment, the securing means are configured internally, inside of the applicator valve 30, to prevent a user from removing the applicator valve 30 from the barrel 12. This embodiment may be preferred when the valve syringe is intended to be disposable, composed of an inexpensive material, and comprises only enough composition for a single use.

Figure 7:
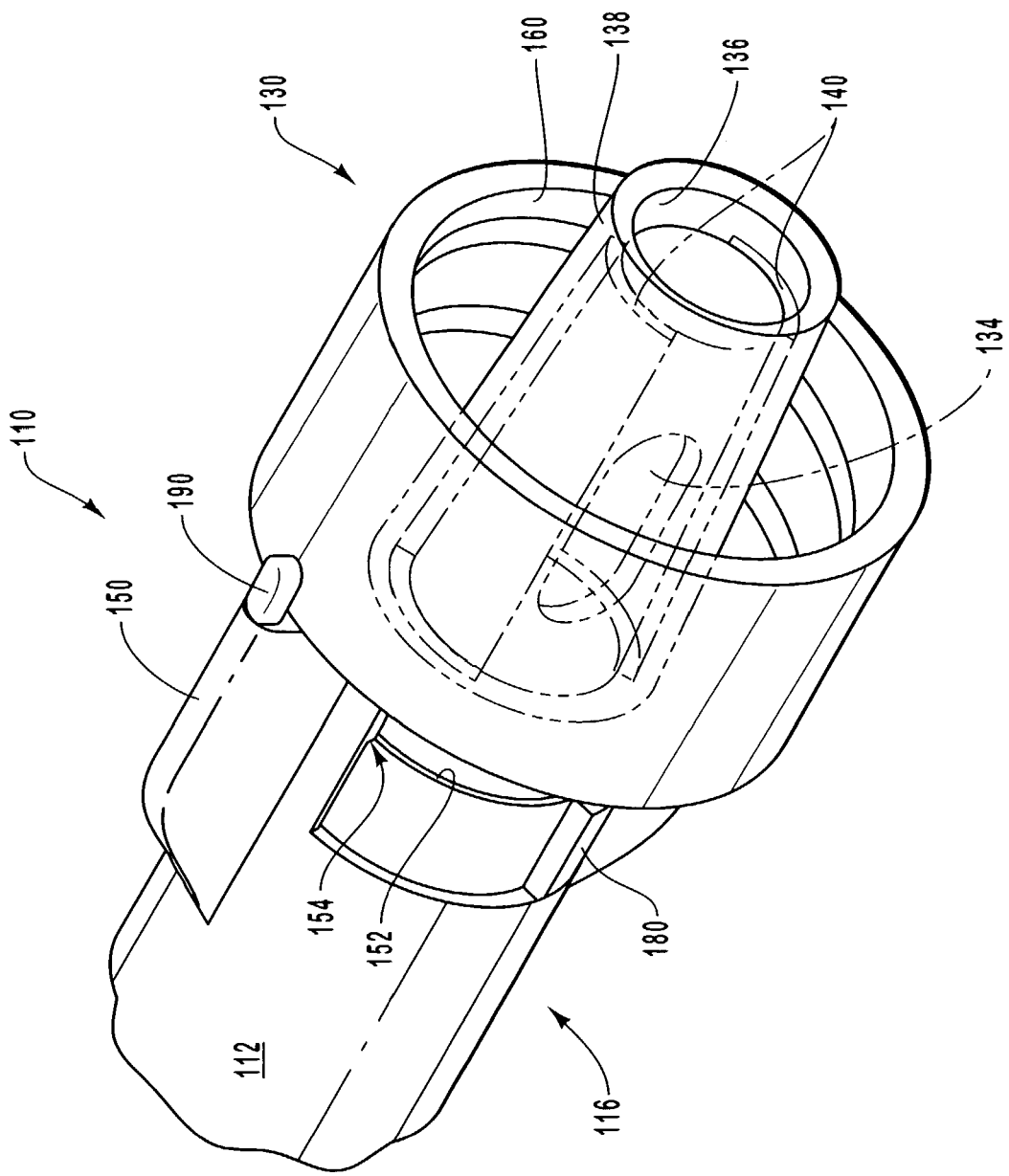
FIG. 7 illustrates an embodiment of an applicator valve of the invention disposed at an outlet end of a syringe barrel in a closed rotational position and which includes threaded coupling means for coupling the applicator valve to a threaded applicator tip.
Figure 8:
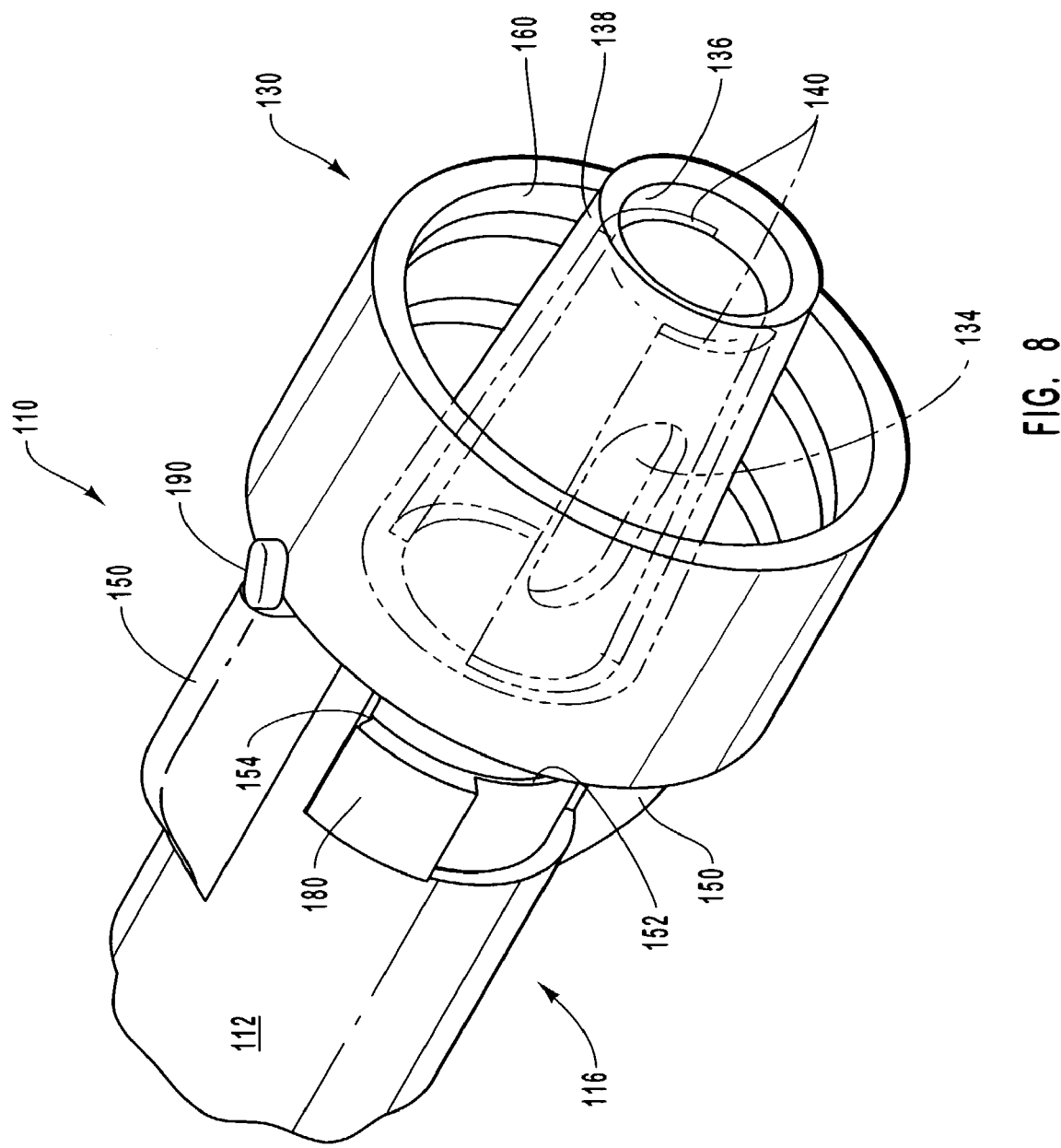
FIG. 8 illustrates an embodiment of an applicator valve of the invention disposed at an outlet end of a syringe barrel in an open rotational position and which includes threaded coupling means for coupling the applicator valve to a threaded applicator tip.
Figure 9:
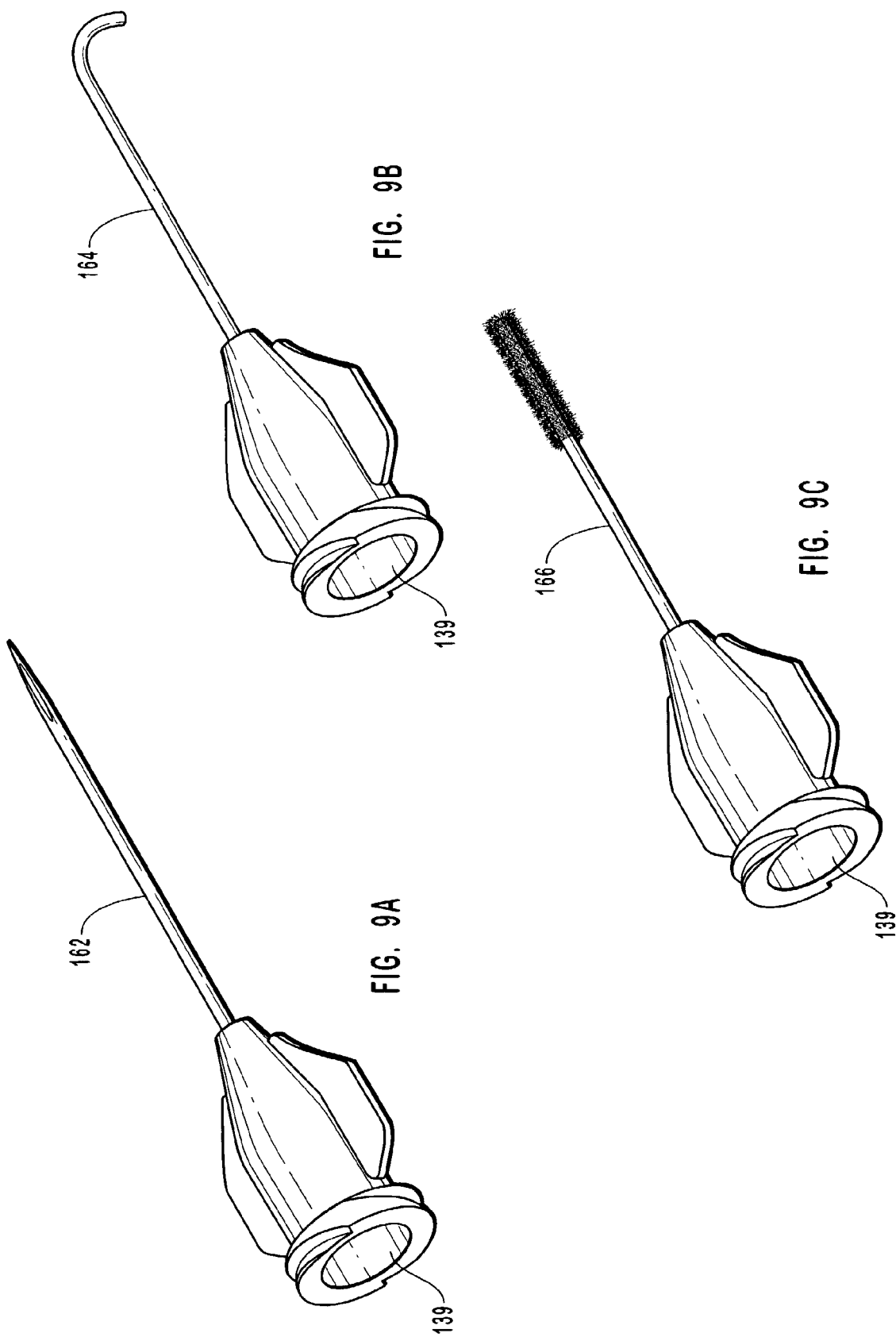
FIG. 9A is a perspective view of an embodiment of an applicator tip of the invention that is threaded and configured as a needle.
FIG. 9B is a perspective view of an embodiment of an applicator tip of the invention that is threaded and configured as a curved cannula.
FIG. 9C is a perspective view of an embodiment of an applicator tip of the t invention that is threaded and includes a flocked surface.

FIGS. 7–9 illustrate an alternative embodiment of the valve syringe 110 of the invention in which the applicator valve 130 is configured with coupling means for coupling the applicator valve 130 to interchangeable applicator tips without removing the applicator valve 130 from the barrel 112 of the valve syringe 110. This embodiment is particularly useful for preventing premature curing in applicator tips between uses.

As shown in FIG. 7, similar to the previous embodiments, the applicator valve 130 includes a contact surface 136 that is configured to block the flow of the fluid material when the applicator valve 130 is in the closed position. As shown in FIG. 7, the applicator valve 130 also includes relief slots 140 that are configured to align with the barrel openings 134 (only one is shown) and to allow the fluid material to flow through the applicator valve 130 when the applicator valve 130 is rotated into the open position, as in the previous embodiments. The valve syringe 110 of the present embodiment also includes retaining means for retaining the applicator valve 130 on the outlet end 116 of the barrel 112. In particular, the valve syringe includes a ridge 152 and corresponding ledges 154 which, as generally described above, slidably engage in a suitable manner for retaining the applicator valve 130 on the outlet end 116 of the barrel 112.

One difference between the present embodiment and the previously disclosed embodiments, however, is that the applicator valve 130 advantageously includes a threaded surface 160 that circumferentially extends around the applicator valve 130 which is configured for threadably engaging and coupling with threaded applicator tips. This threaded surface 160 comprises one suitable coupling means for coupling the applicator valve 130 to interchangeable applicator tips. To accommodate industry standards, the internal mating surface 138 of the applicator valve 130 may be configured with a luer taper.

As shown in FIGS. 9A–9C the applicator tips 162, 164, 166 can include a variety of different configurations, including, but not limited to a needle applicator 162, a curved cannula applicator 164, and a flocked applicator 166. It will be appreciated that the applicator tips can also include other embodiments which are not shown but which are suitably configured to couple with the applicator valve 130 and to dispense the composition contained in the valve syringe during use. The internal mating surface 139 of the applicator tips 162, 164, 166 is preferably configured in size and shape to frictionally engage the mating internal surface 138 of the applicator valve 130, described above.

Figure 10:
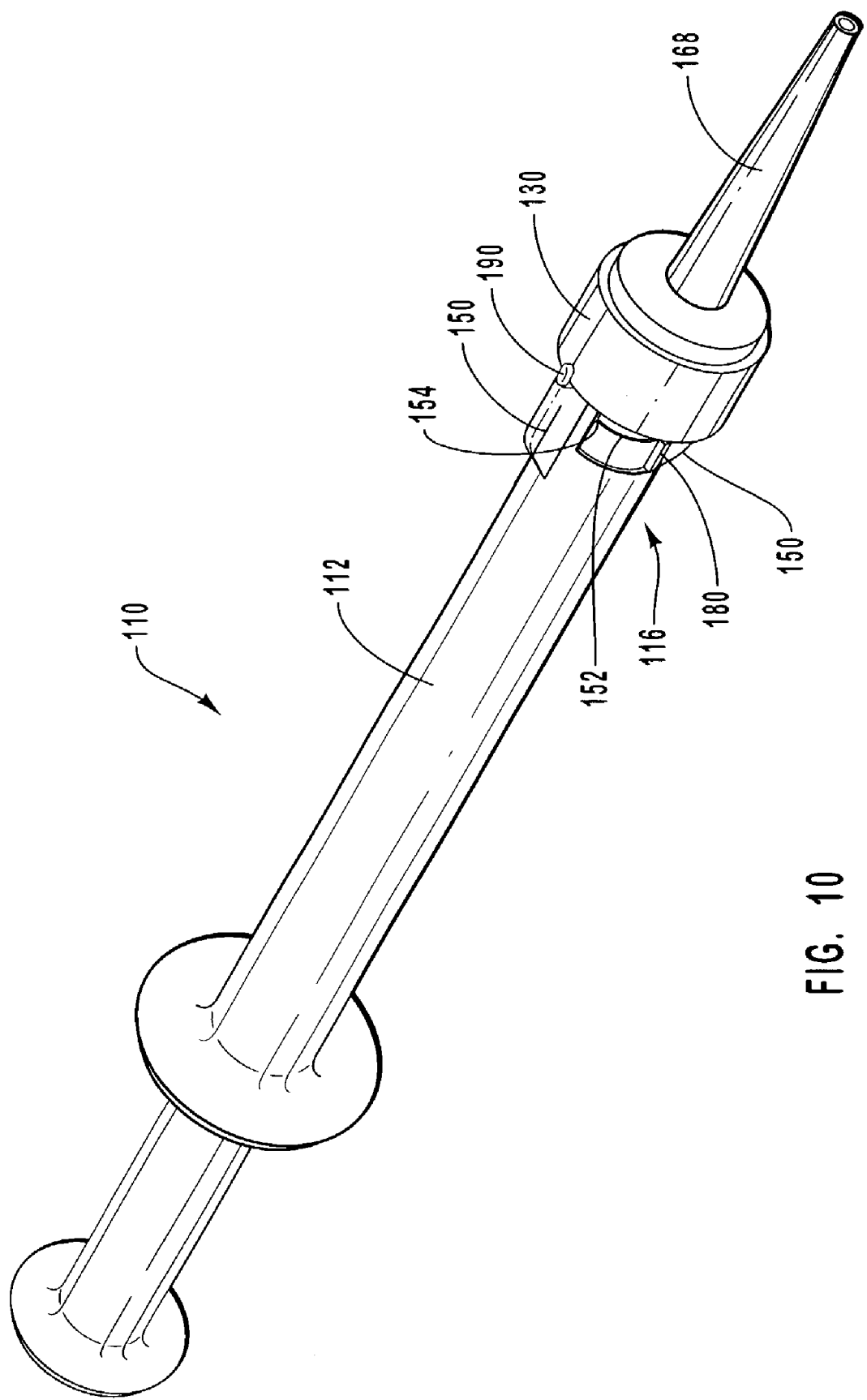
FIG. 10 is a perspective view of an embodiment of the invention in which a valve syringe interconnects an applicator tip to the barrel of the syringe.

FIG. 10 illustrates one embodiment of the valve syringe 110 in which an applicator tip 168 is threadably coupled with the applicator valve 130. It will be appreciated that, as in the previous embodiments, the valve syringe 110 of the invention includes retaining means for retaining the applicator valve 130 on the outlet end 116 of the barrel 112. In particular, as shown in FIGS. 7 and 8, the valve syringe 110 includes tab members 150 with ledges 152, only one of which is shown, that are configured to engage the ridge member 154 circumferentially extending around the applicator valve 130. It will be appreciated that the valve syringe 110 may also include securing means comprising mating engagement formations, not shown, for releasably securing the applicator valve 130 in the closed position, as generally described above in reference to the knobs 42 and recesses 44 that are shown in FIG. 5.

The syringe of the present embodiment is preferably configured to contain multiple doses of composition to be used over a period of time on a plurality of applications. This embodiment is useful, for instance, to maximize the cost efficiency of selling, shipping and storing the composition in bulk quantities. Inasmuch as the valve syringe 110 is intended for repeated use, it is useful to provide the valve syringe 110 with the coupling means that have been described for facilitating the ability to interchange the applicator tips between uses and to preserve a desired level of sanitation between uses.

According to other embodiments, as illustrated in FIGS. 1–5, the valve syringes 10 of the invention also include rotation facilitating means for facilitating rotation of applicator valve 30 between the closed and open positions. For instance, according to this embodiment, the valve syringes 10 comprise wing members 70 that extending from the applicator valve 30 and configured to be engaged by the fingers of a user. The wing members 70 enable a user to apply more leverage during rotation of the applicator valve 30. In another embodiment, not shown, the rotation facilitating means includes a frictional surface on the applicator valve 110. To prevent over-rotation of the applicator valve 30 and 130, the valve syringes 10 and 110 may also include stopping means for stopping rotation of the applicator valve 30 and 130 once the applicator valve 30 and 130 is sufficiently rotated into the open and closed positions. As shown in FIGS. 1–4 and 6–9, the stopping means may include one or more radial block members 80 and 180 protruding away from the applicator valves 30 and 130 which are configured to engage the tab members 50 and 150 once the applicator valves 30 and 130 are completely rotated into the open and closed positions.

In yet another embodiment, the valve syringes 10 and 110 of the invention include tamper evident means for indicating whether the applicator valve 30 and 130 has rotated from the closed position to the open position at least one time. For instance, as shown in FIGS. 1 and 3, bridge members 90 fixedly interconnecting the applicator valve 30 and the barrel 12 at the tab members 50 enables a user to visually determine whether the applicator valve 30 has been rotated out of the closed position. The bridge members 90 are noticeably and irreversibly broken, as shown in FIG. 4, when the applicator valve 30 is rotated from the closed position to the open position for the first time.

FIGS. 7 and 8 illustrate one alternative embodiment of how the tamper evident means can be used with the valve syringes of the invention. As shown, the tamper evident means includes a bridge member 190 that interconnect the applicator valve 130 and the barrel 112 at the general location of the tab member 150. According to this embodiment, the bridge member 190 is noticeably and irreversibly broken when the applicator valve 130 is rotated from the closed position to the open position for the first time. Despite the specific examples provided above, however, it should be appreciated that the tamper evident means can include any number of bridge members that interconnect any portions of the barrel 112 and the applicator valve 130 and are not, therefore, necessarily disposed at the general location of the tab members 50 and 150.

Figure 11:
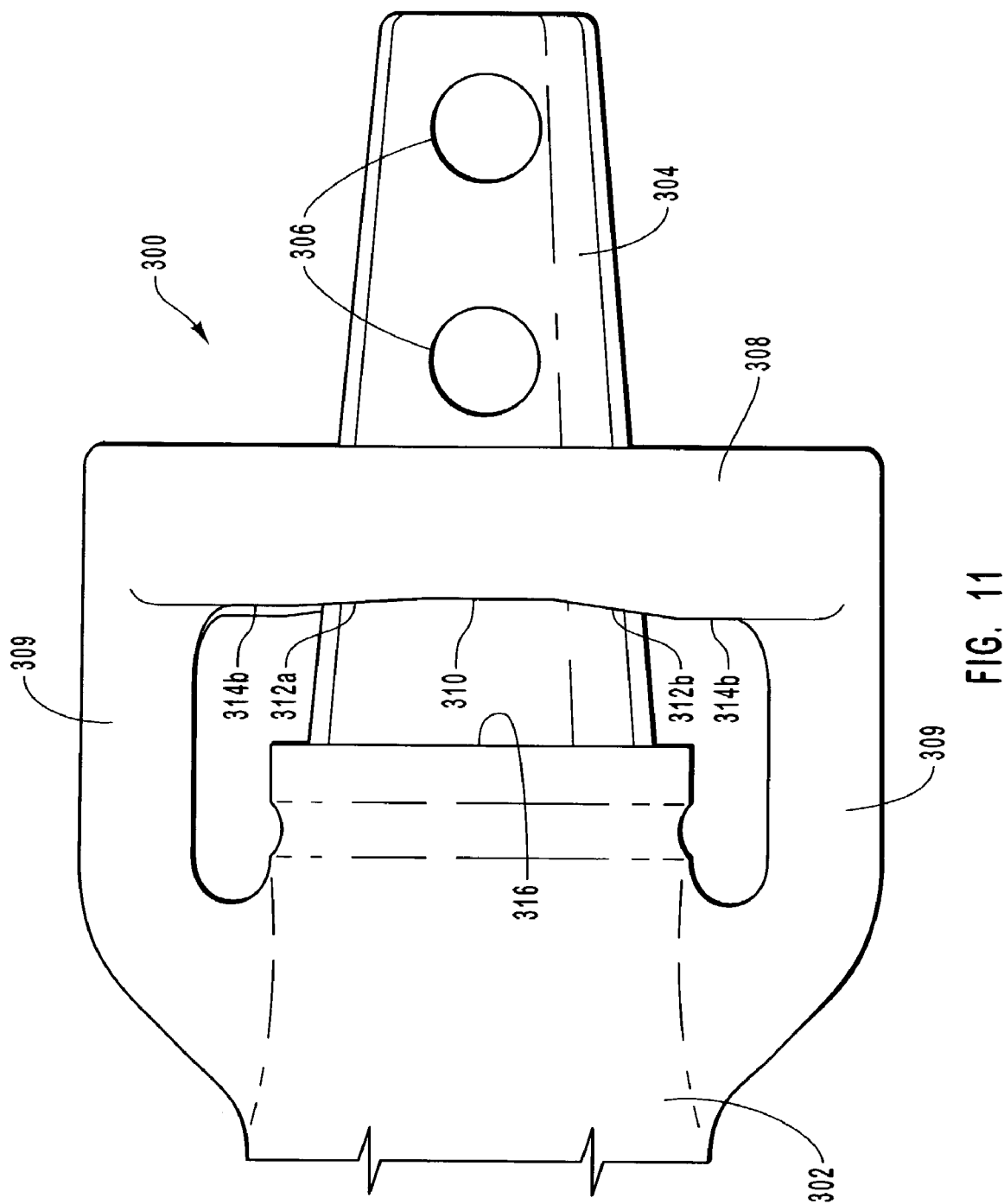
FIG. 11 is a side view of an outlet end of a syringe barrel having a plurality of openings in the outlet end and a circumferential retention ring attached to the barrel by attachment ridges.
Figure 12:
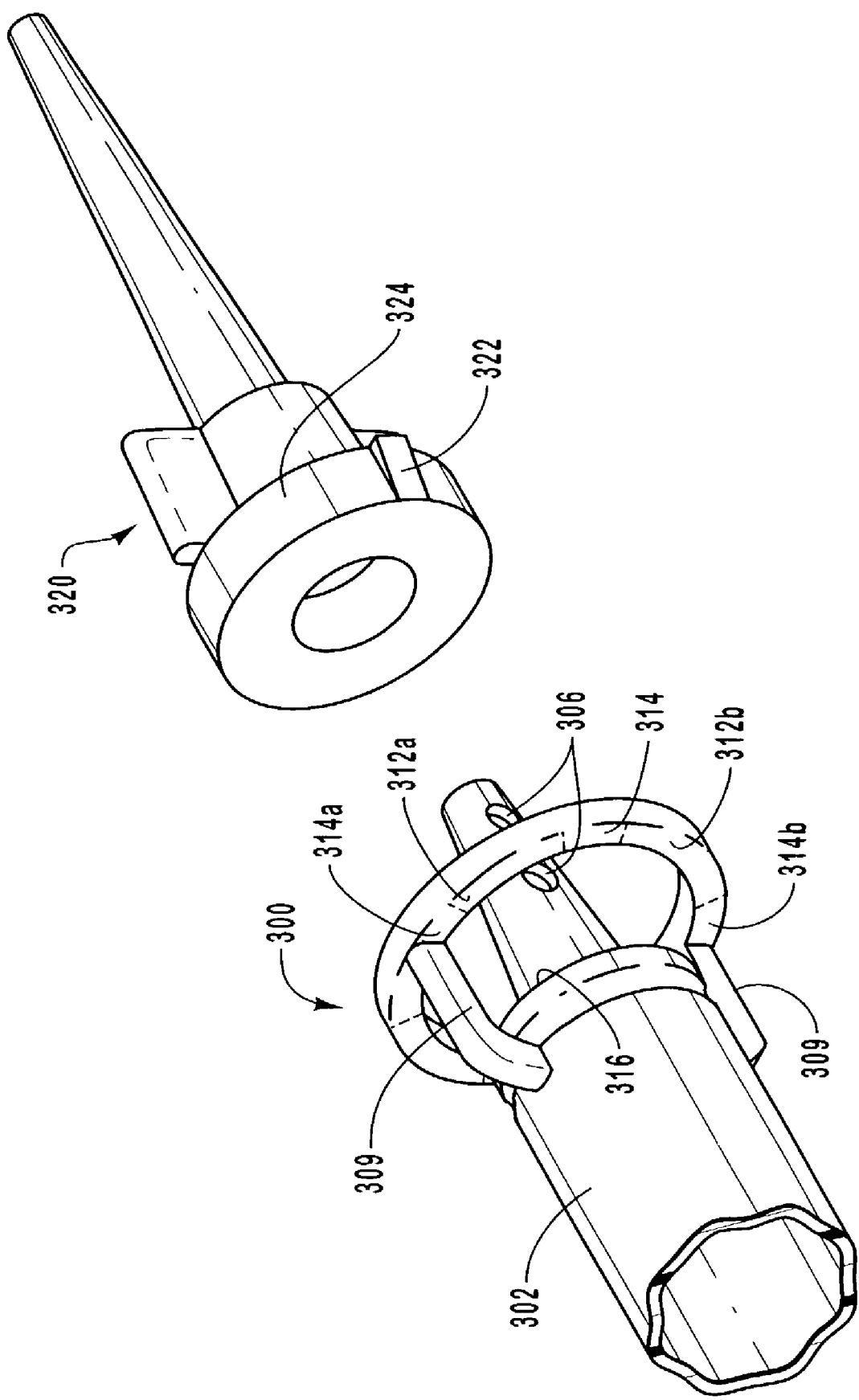
FIG. 12 is an exploded perspective view of the outlet end of the syringe barrel of FIG. 11 and an applicator valve having a lateral protrusion.

FIG. 11 depicts an alternative outlet end 300 of a syringe barrel 302 according to the invention, which includes a tapered sidewall 304 having a plurality of barrel openings 306 on one or both sides of the tapered portion 304 and a circumferential retention ring 308. FIG. 12 is an exploded view depicting the outlet end 300 of the syringe barrel 302 and a corresponding applicator valve 320 that is configured so as to be rotatably coupled to the syringe barrel 302 when the two are joined together.

As best shown in 13A–C, when the applicator valve 320 is joined with the syringe barrel 302, the circumferential retention ring 308 slidably engages one or more protrusions 322 disposed at a proximal end 324 of the applicator valve 320 in order to retain the applicator valve 320 on the outlet end 300 of the syringe barrel 302. Thus, the circumferential retention ring 308 and the one or more protrusions 322 comprise retaining means for retaining the applicator valve 320 on the outlet end 300 of the barrel 302. The lateral protrusions 322 of the applicator valve 320 slidably engage an engagement surface of the circumferential retention ring 308 in order to prevent separation of the applicator valve 320 from the syringe barrel 302. The slidable engagement of the lateral protrusions 322 and the engagement surface of the retention ring 308 allows the applicator valve 320 to be rotated relative to the syringe barrel 302 between opened and closed positions.

As best seen in FIG. 12, the circumferential retention ring 308 is spaced apart from the tapered sidewall 304 by a circumferential gap between the retention ring 308 and the tapered portion 304 through which the one or more lateral protrusions 322 (e.g., two) of the applicator valve 320 are inserted during initial assembly of the valve syringe. The circumferential retention ring 308 is attached to the syringe barrel 302 by a pair of attachment ridges 309 extending from a surface of the outlet end 300 of the barrel 302 and spaced apart by 180°. The attachment ridges 309 may also act as stopping means for engaging the lateral protrusions 322 on the applicator valve 320 in order to limit rotation of the applicator valve 320 relative to the barrel 302. As seen in FIGS. 13B and 13C, respectively, the lateral protrusions 322 of the applicator valve 320 will selectively abut one side of the attachment ridges 309 when the applicator valve 320 is turned to the completely open position (FIG. 13C), and the lateral protrusions 322 will abut the other side of the ridges 309 when the applicator valve 320 is turned to the completely closed position (FIG. 13B).

The engagement surface of the circumferential retention ring 308, together with the lateral protrusions 322 of the applicator valve 320, may also comprise means for varying the sealing engagement between the applicator valve 320 and syringe barrel 302 when the applicator valve 320 is rotated between the open and closed positions. The sealing engagement varying means may comprise a stepped, angled or otherwise varying engagement surface on the circumferential retention ring 308 that engages the lateral protrusions 322 of the applicator valve 320 with varying force as the valve 320 is rotated between the open and closed positions. In this way, the inner surface of the applicator valve 320 is pulled with more or less retention force against the tapered surface 304 of the outlet end 300 of the syringe barrel 302 depending on the rotational position of the lateral protrusions 322 against the engagement surface. This, in turn, varies the sealing engagement between the applicator valve 320 and the syringe barrel 302.

In the embodiment illustrated in FIGS. 11–13, the engagement surface on the circumferential retention ring 308, on each side of the attachment ridges 309, is divided into three sections: a lower-lying middle surface 310, inclined surfaces 312a and 312b extending from each side of the middle region 314, and end surfaces 314a and 314b extending between each inclined section and a respective attachment ridge 309. The lower-lying middle surface 310 is positioned midway between the attachment ridges 309 and is used to facilitate joining of the applicator valve 320 to the outlet end 300 of the syringe barrel 302 during assembly. As the applicator valve 320 is mated with the syringe barrel 302, the retention ring 308 and/or the proximal end 324 of the applicator valve 320 flex slightly in order to allow the lateral protrusions 322 to pass under the retention ring 308 and snap in place in a space between the circumferential retention ring 308 and an end face 316 of the syringe barrel 302. Engagement of the lateral protrusions 322 by the retention ring 308 prevents the applicator valve 320 from detaching from the syringe barrel 302.

When joining the applicator valve 320 to the barrel 302, the lateral protrusions 322 are advantageously aligned with the lower-lying middle surface 310 of the circumferential retention ring 308 in order to provide a degree of play of the lateral protrusions 322 within the space defined by the circumferential retention ring 308 and the end face 316 of the syringe barrel 302 (FIGS. 13A and 13B). This play permits the lateral protrusions 322 to more easily snap in place between the retention ring 308 and proximal face 316 during assembly.

Upon rotating the applicator valve 320 into the closed position, each lateral protrusion 322 engages an inclined surface 312a, which causes the retention ring 308 in this area to pull the inner surface of the applicator valve 320 more tightly against the tapered end 304 of the syringe barrel 304. The tightening of the applicator valve 320 relative to the syringe barrel 304 increases the sealing engagement between the applicator valve 320 and the syringe barrel 302, more particularly the tapered surface 304. When the applicator valve 320 is rotated to the fully closed position (FIG. 13B), each lateral protrusion 322 engages a corresponding end surface 314a of the retention ring 308. The end surfaces 314a are advantageously level, rather than inclined, so as to not act as camming surfaces that might otherwise urge the lateral protrusion 322 to rotate the applicator valve 320 out of the closed position. In another embodiment (not shown), the end surfaces 314a can be stepped relative to the inclined surfaces 312a in order to lock the lateral protrusions 322 against the end surfaces 314a so as to more reliably prevent undesired rotation of the applicator valve 320 out of the closed position. In this embodiment, the lateral protrusions 322 and end surfaces 314a would comprise securing means for releasably securing the applicator valve 320 in the closed position during periods of nonuse.

Upon rotating the applicator valve 320 from the closed position shown in FIG. 13B to the open position shown in FIG. 13C, each lateral protrusion 322 slides down an inclined surface 312a, momentarily crosses through the middle surface 310, and then travels up the opposite inclined surface 312b. This again causes the retention ring 308 in this area to pull the inner surface of the applicator valve 320 more tightly against the tapered end 304 of the syringe barrel 304 so as to increase the sealing engagement of the applicator valve 320 with the syringe barrel 302. When the applicator valve 320 is rotated to the fully open position (FIG. 13C), each lateral protrusion 322 engages a corresponding end surface 314b of the retention ring 308. The end surfaces 314b are advantageously level, rather than inclined, so as to not act as camming surfaces that might otherwise urge the lateral protrusion 322 to rotate the applicator valve 320 out of the open position during use. The opposite end surfaces 310 may optionally be stepped relative to the inclined surfaces 312b in order to lock the lateral protrusions 322 against the end surfaces 314b so as to more reliably prevent undesired rotation of the applicator valve 320 out of the open position. In this embodiment, the lateral protrusions 322 and corresponding end surfaces 314b would comprise securing means for releasably securing the applicator valve 320 in the open position during use.

In one embodiment, the slope of the inclined surface 312b toward the open position might be greater than the slope of the inclined surface 312a toward the closed position in order to create an even tighter seal between the applicator valve 320 and the barrel 302 when the applicator valve 320 is rotated to the open position. This helps prevent leakage of fluid material from between the applicator valve 320 and the syringe barrel 302 as the fluid material is expelled through the outlet end 300 of the barrel 302 by exerting pressure onto a plunger (not shown). This, in turn, provides a safety feature that accounts for deformation of the syringe valve components over time and/or variations in their size.

Some plastics used to manufacture syringe barrels and applicator valves are not entirely rigid, but can elongate or relax over time, particularly when they are stressed while the applicator valve 320 is in the closed position. Because of this, the seal between the applicator valve 320 and syringe barrel 302 may relax over time. Whereas slight relaxation of the seal does not result in leakage of the fluid material when the syringe apparatus is not being used, application of a pressure sufficient to expel the fluid material from the syringe barrel 302 might, in fact, be sufficient to cause fluid material to leak through a seal that has relaxed over time. Providing an inclined surface 312b having a steeper slope than that of the inclined surface 312a increases the seal between the applicator valve 320 and syringe barrel 302 when it is needed most—when the applicator valve 320 is opened to allow fluid material to be expelled from the valve syringe under pressure. In this way, the seal is reliably increased without giving the plastic time to relax in a manner that would relax the seal between the applicator valve 320 and syringe barrel 302. This mechanism may also help offset sealing problems that may arise due to variations in the size of the components used to assemble the valve syringe.

Notwithstanding the foregoing, it will be appreciated that the means for varying the sealing engagement between the syringe barrel and the applicator valve may comprise any arrangement of one or more protrusions and one or more inclined surfaces. For example, the outlet end of the syringe barrel may include one or more inclined surfaces that engage one or more protrusions of the applicator valve in a manner that does not require there to be any gaps or spaces between the structure comprising the inclined surface and the syringe barrel. Conversely, the applicator valve may include a retention ring that engages corresponding protrusions of the syringe barrel. In such an embodiment, the retention ring would turn together with the applicator valve, while the protrusions would remain stationery along with the barrel when the applicator valve is rotated relative to the barrel.

For example, any of the syringes depicted in FIGS. 1–5, 7–8 and 10 can be modified to include one or more sloped surfaces within one or more structures comprising the retaining means (e.g., one or more of the tab members 50, 150, ridge members 52, 152 or ledges 54, 154) in order to cause the sealing engagement between the syringe barrel and applicator valve to vary (e.g., increase) as the valve is rotated toward at least one of the closed or open positions.

Figure 14:
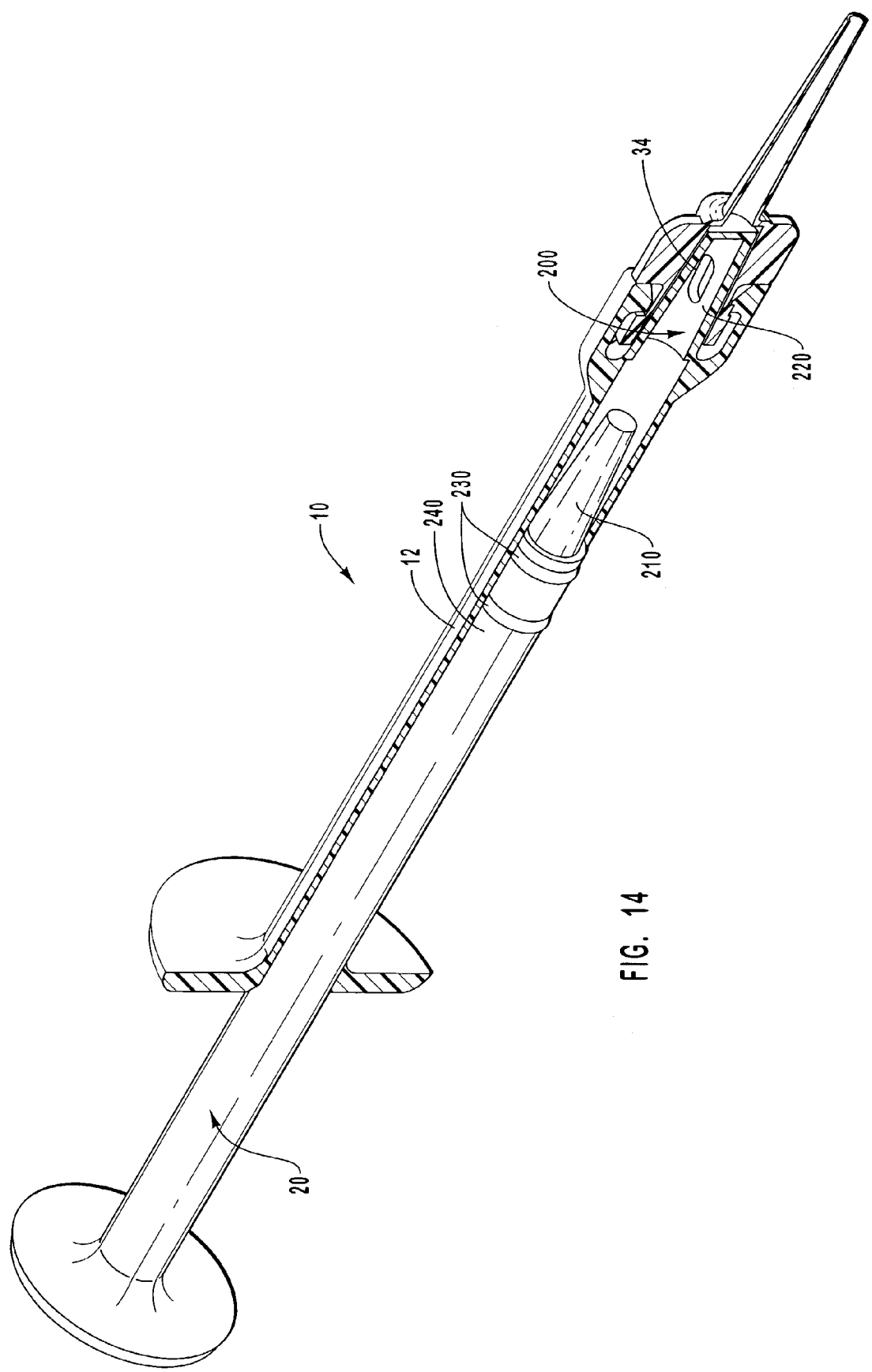
FIG. 14 is a perspective cutaway view of a syringe that includes a syringe barrel having a tapered outlet end and a plunger having a tapered end.

Attention is now directed to FIG. 14, which illustrates a partial cross-sectional view of a syringe 10. As shown, the plunger 20 of the syringe 10 is specifically configured to expel fluid material out of the opening 34 that is formed in the tapered portion 200 of the barrel 12. In particular, the plunger 20 includes a first end 210 that is tapered and configured in size and shape to conformingly engage the inner surface 220 of the tapered portion 200 of barrel 12. The taper of the plunger 20 and the barrel 12 may include a luer taper or any other taper.

The plunger of the invention also includes sealing means for sealing the plunger 20 within the barrel 12. In particular, the plunger 20 includes one or more sealing rings 230 that protrude away from the stem 240 of the plunger 20 and that are located proximate the tapered end 210 of the plunger 20. Accordingly, although the present embodiment illustrates a plunger 20 having two rings 230, it will be appreciated that the plunger 20 can also be configured with a single ring 230 or with more than two rings 230. One benefit of using two or more sealing rings 230 is that the plunger 20 may be more capable of pushing the fluid material through the barrel without allowing any material to leak past the sealing rings 230. A plurality of rings 230 may also provide a greater seal between the stem 240 and the barrel 12, so as to prevent premature leaking and evaporation of the fluid material when the syringe 10 is stored and transported.

The rings 230 are preferably configured to slidably engage the inner surface of the barrel 12 and to create a seal between the stem 240 of the plunger 20 and the barrel 12. This enables the plunger to push the fluid material towards and through the opening formed in the tapered portion 200 of the barrel 12.

Figure 15:
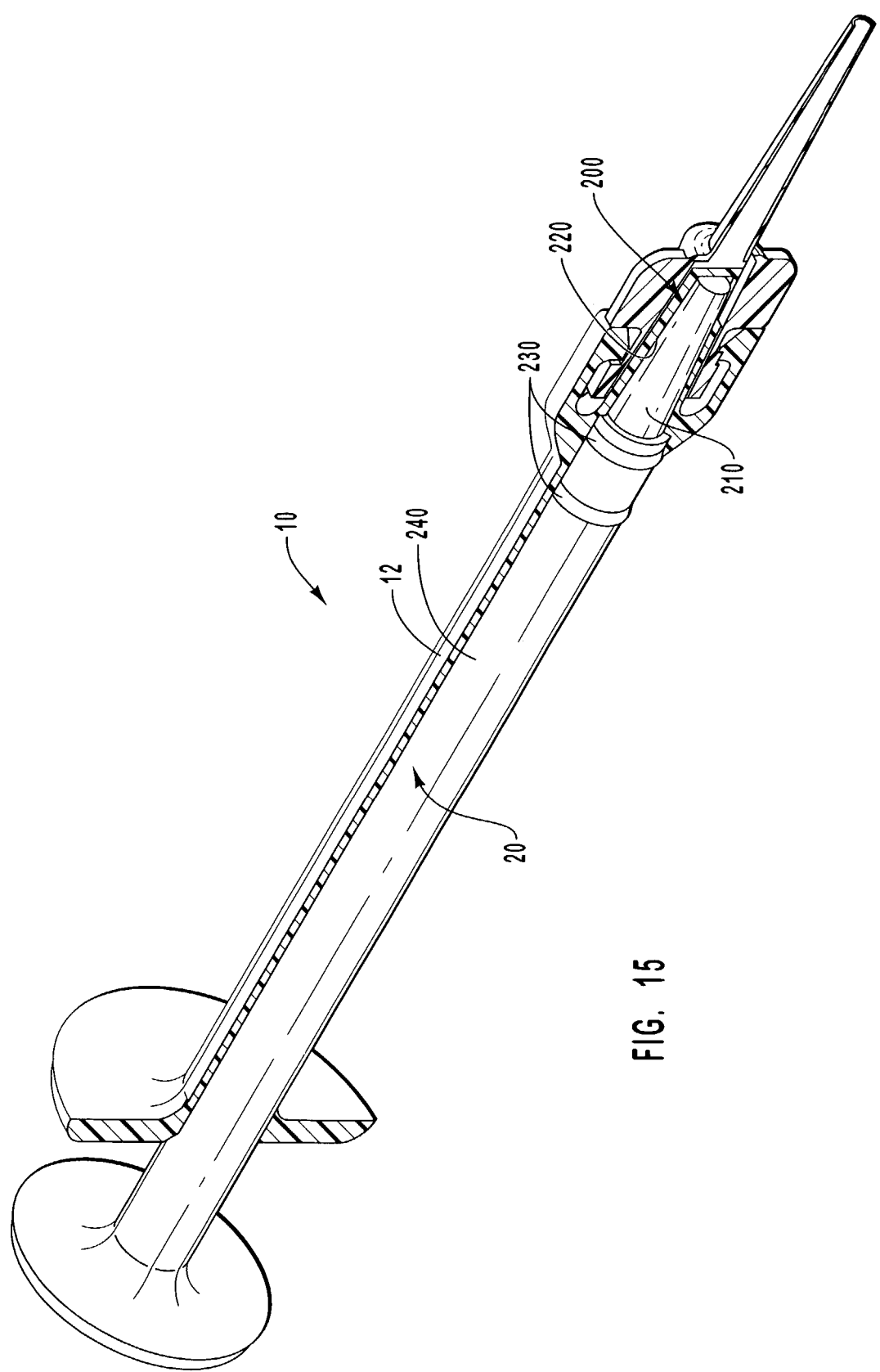
FIG. 15 is a perspective cutaway view of the syringe shown in FIG. 14 in which the plunger is fully inserted within the barrel of the syringe, such that the tapered end of the is Q plunger is inserted within the tapered portion of the barrel.

FIG. 15 illustrates how the tapered end of the plunger 20 is specifically configured to engage the inner surface 220 of the tapered end 200 of the barrel 12. It will be appreciated that this configuration is useful for enabling the plunger 20 to successfully expel substantially all of the fluid material that may be contained within the tapered end 200 of the barrel 12 out of any openings that are formed in the tapered end 200 of the barrel 12, such as the opening 34 that is illustrated in FIG. 14. It will also be appreciated that this configuration is useful for minimizing any wasted product or residual fluid material that would otherwise remain within the barrel 12.

Figure 16:
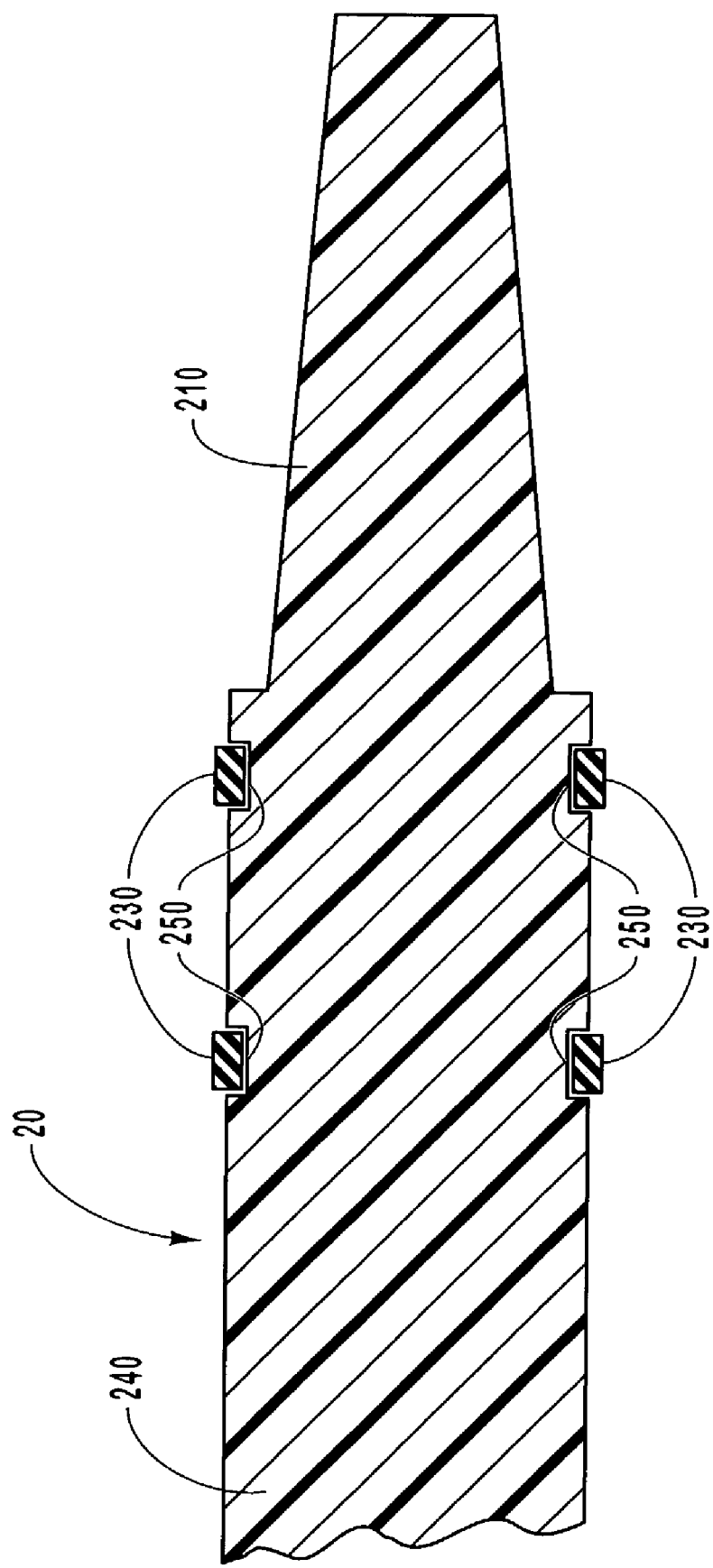
FIG. 16 is a cross-sectional side view of a portion of a syringe plunger having a tapered end and sealing rings disposed about the stem of the plunger.

FIG. 16 illustrates a cross-sectional side view of a portion of the plunger 20 that shows the tapered end 210 and sealing rings 230 of the plunger 20. As shown, the sealing rings 230 may be detachably attached to the stem 240 of the plunger 20. For instance, in the present embodiment, the rings are detachably secured to the stem 240 of the plunger 20 within recesses 250 that are formed in the stem 240. It will be appreciated, however, that the rings 230 may also be integrally formed or attached to the stem 240 such as with a twocolor injection molding process in which the rings 230 are fixedly molded to the stem 240.

Although the rings 230 are shown to have a substantially rectilinear cross-sectional area, it will also be appreciated that the rings 230 can be formed with round, angled or irregular cross-sectional areas. The material of the sealing rings 230 may comprise the same material that is used to form the stem 240 or a different material. According to one embodiment, the sealing rings 230 are composed of a flexible or a semi-rigid plastic or elastomeric material. It will be appreciated, however, that the material composition of the rings 230 may comprise any material that is suitable for creating a seal between the stem 240 and the barrel 12. Non-limiting examples of materials that may be used to manufacture the sealing rings 230 include polyethylene, polypropylene, nylon, Teflon, polycarbonate, natural or synthetic rubber, silicone, other elastomers, and thermoset plastics.

During use, the plunger is forced through the barrel, towards the outlet end of the barrel, causing the fluid material to be expelled out of the opening formed in the outlet end of the barrel. While the plunger is forced through the barrel, the sealing rings slidably engage the inner surface of the barrel, forcing the fluid material forward, preventing leaking of the fluid material between the stem and the barrel. Then, once the tapered end of the plunger is finally inserted into the tapered outlet portion of the barrel, the tapered end of the plunger is able to completely expel any residual amounts of the fluid material that may remain within the tapered portion of the barrel.

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A valve syringe comprising:
    a barrel configured for containing a fluid material, the barrel including an inlet end and an outlet end, the outlet end including a sidewall with at least one outlet opening formed in the sidewall through which fluid material can pass; and
    an applicator valve having an inner contact surface and at least one relief slot formed in the inner contact surface, the applicator valve being rotatably disposed on the outlet end of the barrel so as to be selectively rotatable between an open position, in which the at least one relief slot is at least partially aligned with the at least one outlet opening, and a closed position, in which the inner contact surface of the applicator valve occludes the at least one outlet opening.

2. A valve syringe as recited in claim 1, further comprising a plunger adapted to selectively expel fluid material contained in the barrel through the outlet end.

3. A valve syringe as recited in claim 1, the applicator valve further comprising:
    an applicator tip configured to dispense fluid material, and
    a hollow body configured to channel fluid material from the at least one relief slot to the applicator tip.

4. A valve syringe as recited in claim 1, wherein the sidewall of the outlet end of the barrel and the inner contact surface of the applicator valve comprise luer tapers.

5. A valve syringe as recited in claim 1, further comprising retaining means for retaining the applicator valve applicator valve on the outlet end of the barrel.

6. A valve syringe as recited in claim 5, the retaining means comprising:
    a retention ring connected to the outlet end of the barrel and having an engagement surface; and
    at least one protrusion extending from an end of the applicator valve and adapted to slidably engage the engagement surface of the retention ring so as to maintain the applicator valve and the barrel in a sealing engagement.

7. A valve syringe as recited in claim 6, the engagement surface of the retention ring further comprising at least one inclined surface so that, as the protrusion of the applicator valve is slidably moved along the inclined surface, the sealing engagement between the applicator valve and the barrel is varied.

8. A valve syringe as recited in claim 6, the engagement surface of the retention ring further comprising:
    at least one lower-lying middle surface that defines a localized region of increased space between the end face of the barrel and the engagement surface of the retention ring; and
    one or more inclined surfaces adjacent to the middle surface that are adapted so as to increase the sealing engagement between the applicator valve and the barrel as the applicator valve is rotated so as to slidably move the protrusion along the one or more inclined surfaces away from the middle surface.

9. A valve syringe as recited in claim 6, wherein the engagement surface comprises:
    a first inclined surface along which the protrusion of the applicator valve slides as the applicator valve is moved toward the closed position; and
    a second inclined surface along which the protrusion slides as the applicator valve is moved toward the open position.

10. A valve syringe as recited in claim 9, wherein the first inclined surface is adapted so that the sealing engagement between the applicator valve and the barrel increases to a first amount when the applicator valve is moved to a completely closed position and wherein the second inclined surface is adapted so that the sealing engagement between the applicator valve and the barrel increases to a second amount that is greater than the first amount when the applicator valve is moved to a completely open position.

11. A valve syringe as recited in claim 10, wherein the engagement surface further comprises a first end surface that engages the protrusion when the applicator valve is in the completely closed position and a second end surface that engages the protrusion when the applicator valve is in the completely open position.

12. A valve syringe as recited in claim 11, wherein the first and second end surfaces are not inclined.

13. A valve syringe as recited in claim 11, wherein the first end surface is stepped relative to the first inclined surface in order to releasably lock the applicator valve in the closed position and wherein the second end surface is stepped relative to the second inclined surface in order to releasably lock the applicator valve in the open position.

14. A valve syringe as recited in claim 6, the retention ring being positioned relative to the outlet end of the barrel so as to define a space between an end face of the barrel and the engagement surface, the at least one protrusion of the applicator valve being slidably disposed within the longitudinal space.

15. A valve syringe as recited in claim 14, wherein the retention ring is connected to the outlet end of the barrel by two attachment ridges spaced apart by 180°.

16. A valve syringe as recited in claim 15, wherein the attachment ridges provide stops that limit rotation of the applicator valve between the open and closed positions.

17. A valve syringe comprising:
    a barrel configured for containing a fluid material, the barrel including an inlet end and an outlet end, the outlet end including an end face, a sidewall extending from the end face, and at least one opening in the sidewall through which fluid material can pass;

a retention ring connected to the outlet end of the barrel and having an engagement surface;

an applicator valve having an inner contact surface and at least one relief slot formed in the inner contact surface; and at least one protrusion that extends laterally from an end of the applicator valve and that engages the engagement surface of the retention ring so as to maintain the applicator valve and the barrel in a sealing engagement, the applicator valve being rotatably disposed on the outlet end of the barrel so as to be selectively rotatable between an open position, in which the at least one relief slot is at least partially aligned with the at least one outlet opening, and a closed position, in which the inner contact surface of the applicator valve occludes the at least one outlet opening.

18. A valve syringe as recited in claim 17, further comprising means for varying the sealing engagement between the applicator valve and the syringe barrel.

19. A valve syringe as recited in claim 17, wherein the means for varying the sealing engagement comprises at least one inclined surface within the engagement surface.

20. A valve syringe as recited in claim 17, further comprising securing means for releasably securing the applicator valve in at least one of the closed position or open position.

21. A valve syringe as recited in claim 17, further comprising stopping means for stopping further rotation of the applicator valve when moved to at least one of a completely closed position or a completely open position.

22. A valve syringe comprising:

a barrel configured for containing a fluid material, the barrel including an inlet end and an outlet end, the outlet end including a sidewall with at least one outlet opening formed in the sidewall through which fluid material can pass;

an applicator valve having an inner contact surface and at least one relief slot formed in the inner contact surface, the applicator valve being rotatably disposed on the outlet end of the barrel so as to be selectively rotatable between an open position, in which the at least one relief slot is at least partially aligned with the at least one outlet opening, and a closed position, in which the inner contact surface of the applicator valve occludes the at least one outlet opening; and means for varying sealing engagement between the applicator valve and the barrel.

23. A valve syringe as defined in claim 22, wherein the means for varying sealing engagement comprises at least one inclined surface associated with the barrel that is configured to engage at least one protrusion of the applicator valve.

24. A valve syringe as defined in claim 22, wherein the means for varying sealing engagement comprises at least one inclined surface associated with the applicator valve that is configured to engage at least one protrusion of the barrel.

25. A valve syringe as defined in claim 22, wherein the means for varying sealing engagement comprises a retention ring attached to a proximal end of the applicator valve and at least one protrusion that laterally extends from the outlet and the barrel that is adapted to slidably engage the retention ring of the applicator valve.

* * * * *

UNITED STATES PATENT AND TRADEMARK OFFICE
CERTIFICATE OF CORRECTION

PATENT NO. : 7,198,619 B2  Page 1 of 1
APPLICATION NO. : 10/397545
DATED : April 3, 2007
INVENTOR(S) : Bills et al.

It is certified that error appears in the above-identified patent and that said Letters Patent is hereby corrected as shown below:

Column 2
Line 21, change "Utip" to --tip--

Column 5
Line 44, change "the t invention" to --the invention--

Column 6
Line 9, after "the" delete "is Q"
Line 44, change "about six v," to --about six,--

Column 7
Line 38, after "opening" add --34--

Column 10
Line 26, change "extending" to --extend--

Column 14
Line 56, change "twocolor" to --two-color--

Column 15
Line 57, after "applicator valve" delete "applicator"
Line 58, delete "valve"

Signed and Sealed this

Twenty-seventh Day of November, 2007

JON W. DUDAS
*Director of the United States Patent and Trademark Office*